United States Patent
Murphy et al.

(10) Patent No.: US 11,998,290 B2
(45) Date of Patent: *Jun. 4, 2024

(54) OCCLUSION TRAVERSAL ROBOTIC CATHETER SYSTEM

(71) Applicant: Corindus, Inc., Waltham, MA (US)

(72) Inventors: John Murphy, North Reading, MA (US); Tal Wenderow, Newton, MA (US)

(73) Assignee: Corindus, Inc., Newton, MA (US)

( * ) Notice: Subject to any disclaimer, the term of this patent is extended or adjusted under 35 U.S.C. 154(b) by 440 days.

This patent is subject to a terminal disclaimer.

(21) Appl. No.: 17/444,571

(22) Filed: Aug. 6, 2021

(65) Prior Publication Data

US 2021/0361366 A1 Nov. 25, 2021

Related U.S. Application Data

(63) Continuation of application No. 16/267,832, filed on Feb. 5, 2019, now Pat. No. 11,109,919, which is a
(Continued)

(51) Int. Cl.
*A61B 34/30* (2016.01)
*A61B 17/22* (2006.01)
(Continued)

(52) U.S. Cl.
CPC ...... *A61B 34/30* (2016.02); *A61B 17/320758* (2013.01); *A61B 90/98* (2016.02);
(Continued)

(58) Field of Classification Search
CPC ... A61B 34/30; A61B 2034/301; A61B 17/22; A61B 17/320758; A61B 17/320725;
(Continued)

(56) References Cited

U.S. PATENT DOCUMENTS 4,706,671 A 11/1987 Weinrib
4,926,858 A 5/1990 Gifford et al.
(Continued)

FOREIGN PATENT DOCUMENTS

WO 2007005976 A1 1/2007
WO 2010025338 A1 3/2010

OTHER PUBLICATIONS

EESR for EP Application 11833036.4; mail date Jun. 30, 2017; 12 pages.
(Continued)

*Primary Examiner* — Robert A Lynch

(57) ABSTRACT

A robotic catheter procedure system for performing a procedure to treat a vascular lesion including a bedside system and a remote workstation is provided. The bedside system includes a first percutaneous device including an end section, the end section structured to allow the first percutaneous device to create a bore through the vascular lesion. The bedside system includes a second percutaneous device. The bedside system also includes a first actuating mechanism configured to engage and to impart movement to the first percutaneous device and a second actuating mechanism configured to engage and to impart movement to the second percutaneous device. The remote workstation includes a user interface and a control system operatively coupled to the user interface and to the bedside system. The control system controlling the first actuating mechanism to cause movement of the first percutaneous device to create a bore through the lesion and the second actuating mechanism to cause movement of the second percutaneous device through the bore created by the first percutaneous device.

20 Claims, 11 Drawing Sheets

Related U.S. Application Data continuation of application No. 13/862,388, filed on Apr. 13, 2013, now Pat. No. 10,238,456, which is a continuation of application No. PCT/US2011/053642, filed on Sep. 28, 2011.

(60) Provisional application No. 61/393,154, filed on Oct. 14, 2010.

(51) Int. Cl.
*A61B 17/3207* (2006.01)
*A61B 18/02* (2006.01)
*A61B 18/14* (2006.01)
*A61B 90/98* (2016.01)
*A61M 25/01* (2006.01)

(52) U.S. Cl.
CPC ............... *A61M 25/0158* (2013.01); *A61B 2017/22042* (2013.01); *A61B 2017/22044* (2013.01); *A61B 2017/22094* (2013.01); *A61B 17/320725* (2013.01); *A61B 2018/0212* (2013.01); *A61B 18/1492* (2013.01); *A61B 2034/301* (2016.02)

(58) Field of Classification Search
CPC .... A61B 17/32002; A61B 2017/22042; A61B 2017/22044; A61B 2017/22094; A61B 2017/320004; A61B 2017/320008; A61B 2017/320733; A61B 2017/320741; A61B 18/1492; A61B 2018/0212; A61B 19/2203; A61B 2019/2219; A61B 2019/2269; A61B 90/98; A61M 25/0158

See application file for complete search history.

(56) References Cited

U.S. PATENT DOCUMENTS

| | | | |
|---|---|---|---|
| 5,217,474 A | 6/1993 | Zacca et al. | |
| 6,156,046 A | 12/2000 | Passafaro et al. | |
| 10,238,456 B2 * | 3/2019 | Murphy | A61B 34/30 |
| 11,109,919 B2 * | 9/2021 | Murphy | A61B 34/30 |
| 2004/0147934 A1 | 7/2004 | Kiester | |
| 2005/0119615 A1 | 6/2005 | Noriega et al. | |
| 2005/0165431 A1 | 7/2005 | Krivoruchko | |
| 2006/0074442 A1 | 4/2006 | Noriega et al. | |
| 2006/0195137 A1 | 8/2006 | Sepetka et al. | |
| 2008/0161801 A1 | 7/2008 | Steinke et al. | |
| 2010/0010505 A1 | 1/2010 | Herlihy et al. | |
| 2010/0175701 A1 | 7/2010 | Reis et al. | |
| 2010/0274087 A1 | 10/2010 | Diolaiti et al. | |
| 2011/0237880 A1 | 9/2011 | Hamel et al. | |
| 2014/0277002 A1 | 9/2014 | Grace | |

OTHER PUBLICATIONS

International Preliminary Report on Patentability for PCT/US2011/053642; dated Apr. 25, 2013; 12 pages.
International Search Report and Written Opinion for PCT/US2011/053642; dated Jan. 17, 2012; 14 pages.
Extended European Search Report for Corresponding EP Application No. 23206820.5, dated Feb. 20, 2024.

* cited by examiner

OCCLUSION TRAVERSAL ROBOTIC CATHETER SYSTEM

CROSS-REFERENCE TO RELATED APPLICATIONS

This application is a continuation of U.S. patent application Ser. No. 16/267,832, filed Feb. 5, 2019, which is a continuation of U.S. patent application Ser. No. 13/862,388, filed Apr. 13, 2013, now U.S. Pat. No. 10,238,456, which is a continuation of International Application No. PCT/US11/53642, filed Sep. 28, 2011, which claims priority to the benefit of priority under 35 U.S.C. § 119(e) of U.S. Provisional Application No. 61/393,154, having a filing date of Oct. 14, 2010, titled "Occlusion Traversal Robotic Catheter System," the complete disclosures of all are hereby incorporated by reference in their entirety.

BACKGROUND

The present invention relates generally to the field of catheter systems for performing diagnostic and/or intervention procedures. The present invention relates specifically to catheter systems and methods related to occlusion traversal by a percutaneous device.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY

One embodiment of the invention relates to a robotic catheter procedure system for performing a procedure to treat a vascular lesion including a bedside system and a remote workstation. The bedside system includes a first percutaneous device including an end section, the end section structured to allow the first percutaneous device to create a bore through the vascular lesion. The bedside system includes a second percutaneous device. The bedside system also includes a first actuating mechanism configured to engage and to impart movement to the first percutaneous device and a second actuating mechanism configured to engage and to impart movement to the second percutaneous device. The remote workstation includes a user interface and a control system operatively coupled to the user interface and to the bedside system. The control system controlling the first actuating mechanism to cause movement of the first percutaneous device to create a bore through the lesion and the second actuating mechanism to cause movement of the second percutaneous device through the bore created by the first percutaneous device.

Another embodiment of the invention relates to a cassette for use with a robotic catheter system configured to couple to a base. The cassette includes a housing, a guide wire including a helical end section structured to create a bore through a vascular lesion, and a second percutaneous device. The cassette also includes a first actuating mechanism configured to engage and to impart axial movement and rotational movement to the guide wire to create the bore through the lesion and a second actuating mechanism configured to engage and to impart axial movement to the second percutaneous device to advance the second percutaneous device through the bore created by the first percutaneous device. The first actuating mechanism and the second actuating mechanism are configured to be operatively coupled to at least one actuator that provides energy to move the guide wire and the second percutaneous device.

Another embodiment of the invention relates to a method for operating a robotic catheter system during treatment of a vascular lesion within a patient including providing a robotic catheter system. The robotic catheter system includes a first guide wire and a second guide wire including an end section, the end section structured to allow the second guide wire to create a bore through the vascular lesion. The robotic catheter system includes a percutaneous device, a first actuating mechanism configured to engage and to impart axial movement and rotational movement to the first guide wire and the second guide wire, and a second actuating mechanism configured to engage and to impart axial movement to the percutaneous device. The robotic catheter system also includes at least one control, and the first and second actuating mechanisms are responsive to the operation of the at least one control by the user. The method includes engaging the first guide wire with the first actuating mechanism and engaging the percutaneous device with the second actuating mechanism. The method includes operating the at least one control to advance the first guide wire to the vascular lesion via the first actuating mechanism and operating the at least one control to advance the percutaneous device along the guide wire to the vascular lesion via the second actuating mechanism. The method includes operating the at least one control to retract the first guide wire out of the patient via the first actuating mechanism and disengaging the first guide wire from the first actuating mechanism. The method includes engaging the second guide wire with the first actuating mechanism and operating the at least one control to advance the second guide wire to create a bore through the vascular lesion. The method includes operating the at least one control to advance the percutaneous device through the bore created by the second guide wire and treating the vascular lesion with the percutaneous device.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
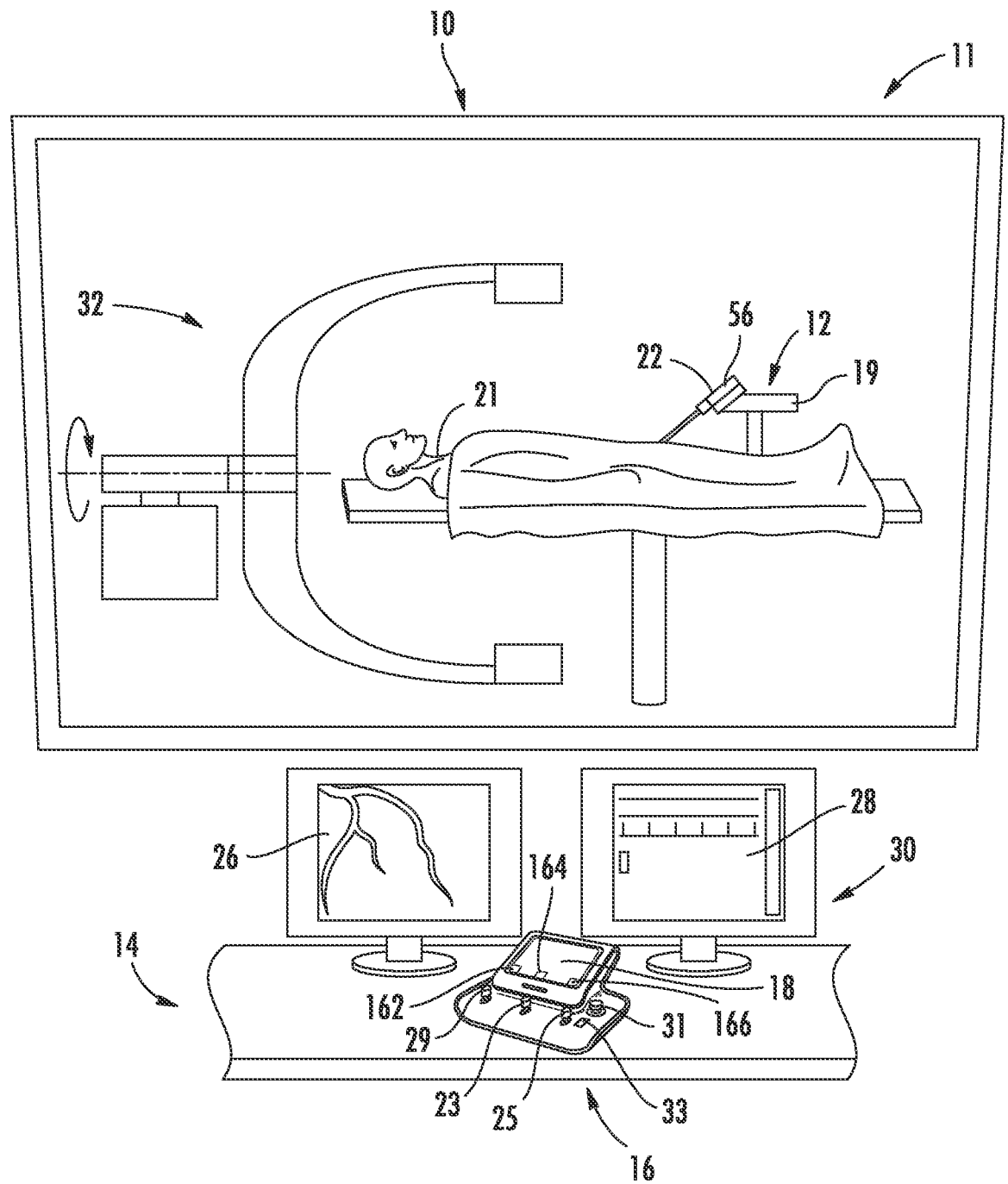
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, such as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter based medical procedure via a robotic system by operating various controls such as the controls located at workstation 14. Bedside system 12 may include any number and/or combination of components to provide bedside system 12 with the functionality described herein. Bedside system 12 may include a cassette 56 coupled to a base 19, and cassette 56 may include a housing 22 that supports the various components of the cassette. Various embodiments of bedside system 12 and cassette 56 are described in detail in P.C.T. International Application No. PCT/US2009/042720, filed May 4, 2009, which is incorporated herein by reference in its entirety.

In one embodiment, bedside system 12 may be equipped to perform a catheter based diagnostic procedure. In this embodiment, bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In this embodiment, bedside system 12 may be equipped with a guide catheter, a guide wire, and a working catheter (e.g., a balloon catheter, a stent delivery catheter, ablation catheter, etc.). In one embodiment, discussed in more detail below, bedside system 12 may be equipped with a guide wire (e.g., an occlusion traversal guide wire) configured to penetrate and/or traverse a blockage located within the vascular system of a patient (e.g., a vascular occlusion, a highly stenotic lesion, etc.). In one embodiment, bedside system 12 may be equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to bedside system 12 to control the various functions of beside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30 configured to receive user inputs to operate various components or systems of catheter procedure system 10. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.). In some embodiments, one or more of the percutaneous intervention devices may be steerable, and controls 16 may be configured to allow a user to steer one or more steerable percutaneous device. In one such embodiment, bedside system 12 may be equipped with a steerable guide catheter, and controls 16 may also be configured to allow the user located at remote workstation 14 to control the bending of the distal tip of a steerable guide catheter.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, retract, or rotate a working catheter, and guide catheter control 29 is a joystick configured to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause the operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient-specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In one embodiment, monitors 26 and/or 28 may be configured to display an image of a portion of the patient (e.g., the patient's heart) at one or more magnification levels. In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. Referring to FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 to properly move and position the percutaneous devices within the 3D geometry of the patient's heart. For example, displaying the proper view during a procedure may allow the user to view a patient's vascular system from the proper angle to ensure that the distal tip of a steerable guide catheter is bent in the proper way to ensure the catheter is moved as intended. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
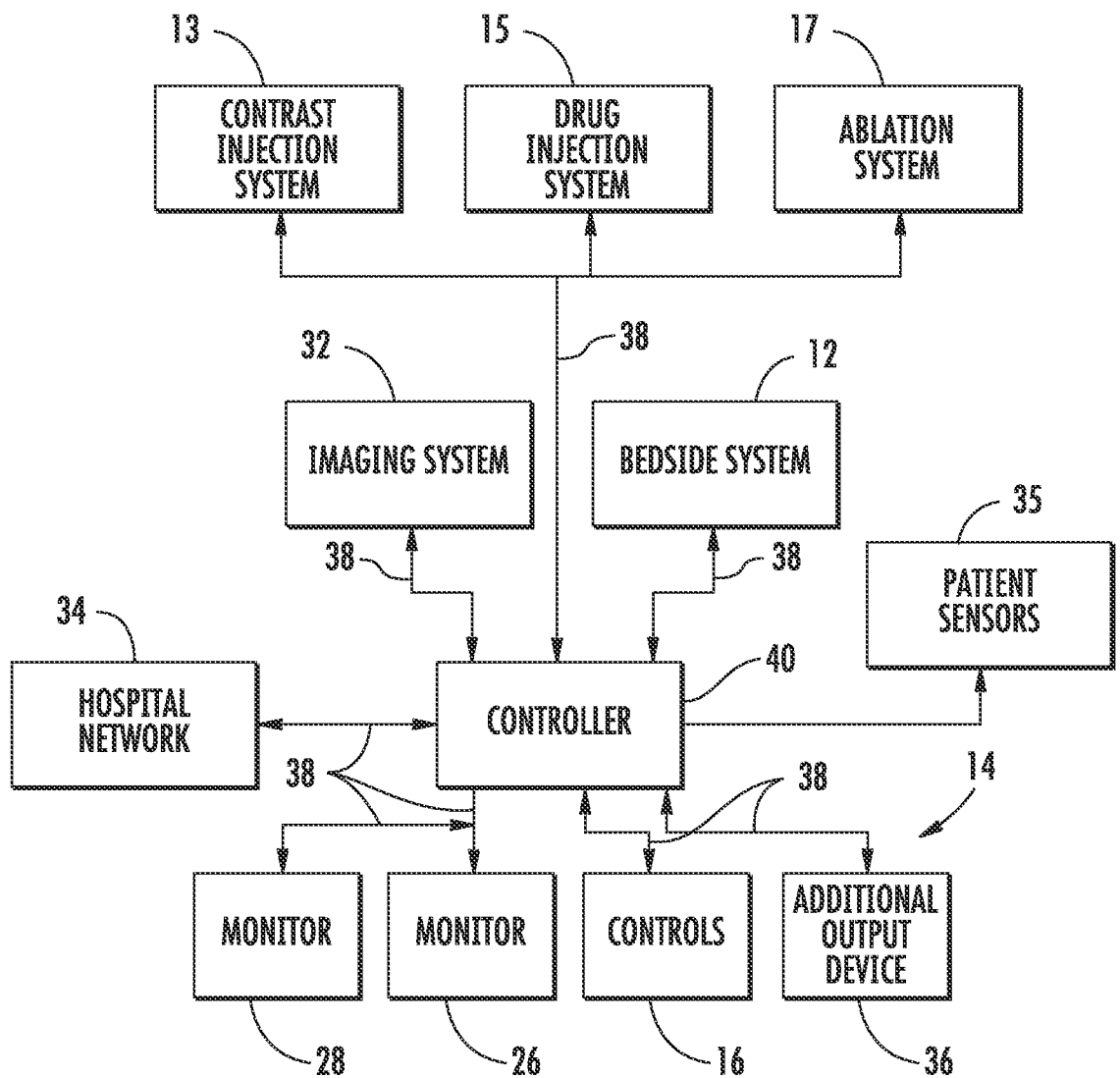
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, such as controller 40. Controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37. Controller 40 may also be in communication with a contrast injection system 13, a drug injection system 15 and an ablation system 17.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, medicine tracking and/or logging systems, user logs, encryption systems, systems to restrict access or use of catheter procedure system 10, robotic catheter systems of the past, present, or future, etc.

Figure 3A:
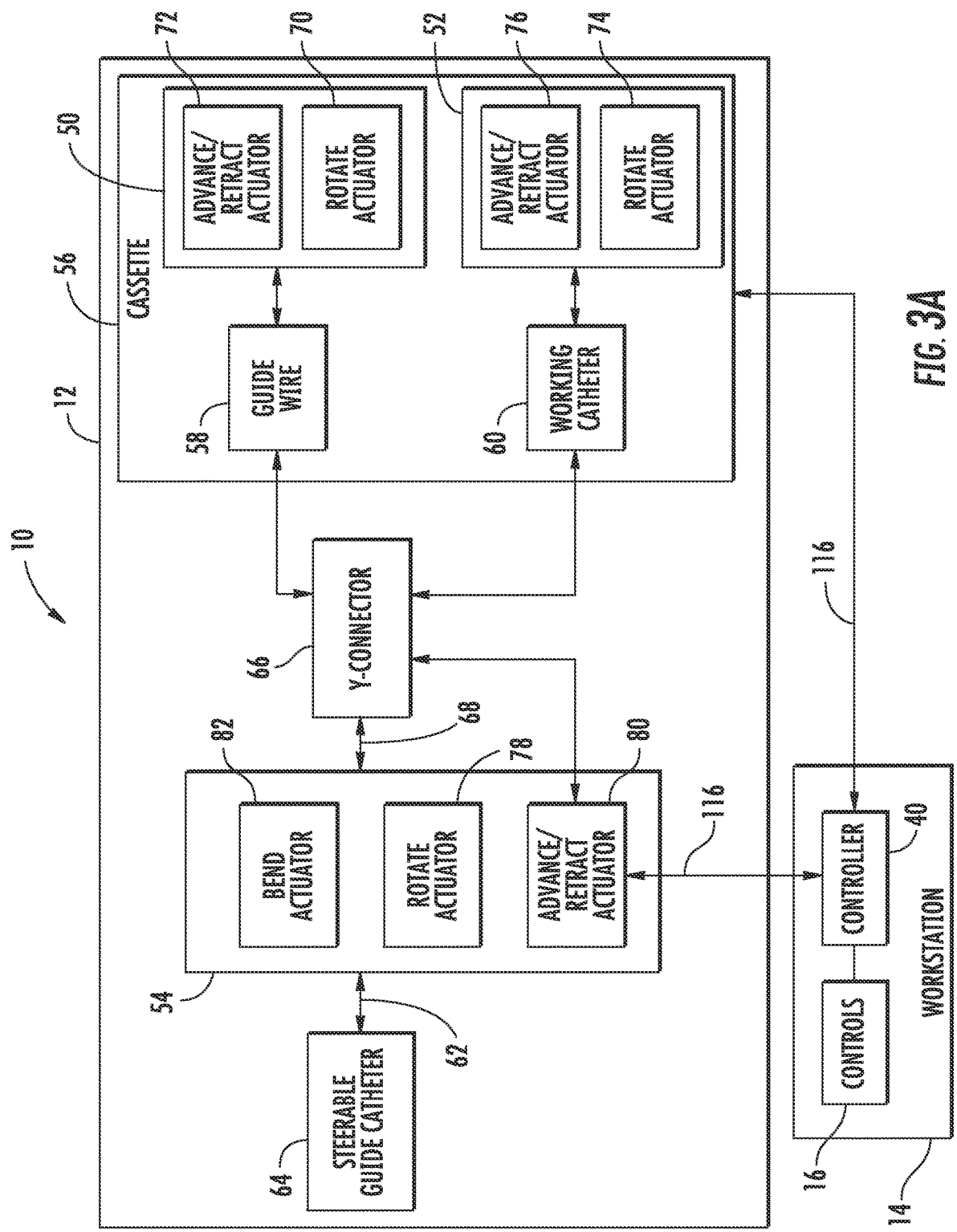
FIG. 3A is a block diagram of a catheter procedure system depicting various actuating mechanisms according to an exemplary embodiment.

Referring to FIG. 3A, a block diagram of an embodiment of catheter procedure system 10 is shown according to an exemplary embodiment. Catheter procedure system 10 may include various actuating mechanisms that engage and impart motion to an associated percutaneous device in response to a user's manipulation of controls 16 and/or under control of controller 40. In one embodiment, catheter procedure system 10 includes a guide wire actuating mechanism 50, a working catheter actuating mechanism 52, and a guide catheter actuating mechanism 54. In other embodiments, catheter procedure system 10 may include an actuating mechanism for inflating an angioplasty or stent delivery balloon and an actuating mechanism for delivering contrast agent. In one embodiment, guide wire actuating mechanism 50 and working catheter actuating mechanism 52 are incorporated within cassette 56. Additional embodiments of bedside system 12 and cassette 56 are described in detail in P.C.T. International Application No. PCT/US2009/042720, filed May 4, 2009, which is incorporated herein by reference in its entirety.

Guide wire actuating mechanism 50 is coupled to guide wire 58 such that guide wire actuating mechanism 50 is able to cause guide wire 58 to advance, retract, and rotate. Working catheter actuating mechanism 52 is coupled to working catheter 60 such that working catheter actuating mechanism 52 is able to cause working catheter 60 to advance, retract, and rotate. Connector 62 couples guide catheter 64 to guide catheter actuating mechanism 54 such that guide catheter actuating mechanism 54 is able to cause guide catheter 64 to advance, retract, and rotate. In various embodiments, guide wire actuating mechanism 50, working catheter actuating mechanism 52, and guide catheter actuating mechanism 54 may each include an engagement structure suitable for engaging the respective percutaneous device such that the actuating mechanism is able to impart axial and/or rotational movement to the percutaneous device.

A Y-connector 66 is coupled to guide catheter actuating mechanism 54 via connector 68. In various embodiments, connector 68 may be a component separate from both Y-connector 66 and guide catheter actuating mechanism 54. In other embodiments, connector 68 may be part of (e.g., integral with) Y-connector 66 or part of actuating mechanism 54. In one embodiment, Y-connector 66 is also connected to cassette 56.

In one embodiment, Y-connector 66 includes a first leg, a second leg, and a third leg. The first leg of the Y-connector is connected to or in communication with the internal lumen of guide catheter 64. The second leg is angled away from the longitudinal axis of guide catheter 64. The second leg provides a port for the injection of fluids (e.g., contrast media, medicine, etc.) into the lumen of guide catheter 64. The third leg of Y-connector 66 is coupled to a cassette 56 and receives both guide wire 58 and working catheter 60. Thus, by this arrangement, guide wire 58 and working catheter 60 are inserted through Y-connector 66 into the internal lumen of guide catheter 64.

Guide wire actuating mechanism 50 includes a rotate actuator 70 and an advance/retract actuator 72. Rotate actuator 70 is configured to cause rotation of guide wire 58 about its longitudinal axis. Advance/retract actuator 72 is configured to advance and/or retract guide wire 58 (i.e., to advance and/or retract along the longitudinal axis of the guide wire) within patient 21. Working catheter actuating mechanism 52 includes a rotate actuator 74 and an advance/retract actuator 76. Rotate actuator 74 is configured to cause rotation of working catheter 60 about its longitudinal axis. Advance/retract actuator 76 is configured to advance and/or retract working catheter 60 (i.e., to advance and/or retract along the longitudinal axis of the working catheter) within patient 21. Guide catheter actuating mechanism 54 includes a rotate actuator 78, an advance/retract actuator 80, and a bend actuator 82. Rotate actuator 78 is configured to cause rotation of guide catheter 64 about its longitudinal axis. Advance/retract actuator 80 is configured to advance and/or retract guide catheter 64 (i.e., to advance and/or retract along the longitudinal axis of the guide catheter) within patient 21. In some embodiments, guide catheter 64 may include one or more bend control elements that allow the user to cause bending of the distal tip of guide catheter 64. In such an embodiment, bend actuator 82 causes the distal tip of guide catheter 64 to bend in response to the user's manipulation of controls 16.

Referring to the block diagram of FIG. 3A, controls 16 and controller 40 located at workstation 14 are communicably coupled to various portions of bedside system 12 to allow the user to control movement of guide wire 58, working catheter 60 and guide catheter 64 and any other percutaneous devices that bedside system 12 is equipped with. Controls 16 and controller 40 are communicably coupled to guide catheter actuating mechanism 54 to allow the user to move guide catheter 64. In addition, controls 16 are communicably coupled to cassette 56 to allow the user to control guide wire 58 via guide wire actuating mechanism 50 and to control working catheter 60 via working catheter actuating mechanism 52. In various embodiments, controller 40 may be configured to provide automated movement of a percutaneous device. In such embodiments, controller 40 may be configured to control the movement of guide wire 58, working catheter 60, and/or guide catheter 64 via guide wire actuating mechanism 50, working catheter actuating mechanism 52, and/or guide catheter actuating mechanism 54, respectively, without requiring the user to specifically instruct movement of the device via controls 16.

In one embodiment, cassette 56 is configured to be coupled to a motor drive base 19 (shown in FIG. 1). In this embodiment, each of the actuators 70, 72, 74, and 76 of cassette 56 are configured to engage capstans extending from the motor drive base. Motors located within the motor drive base drive (e.g., rotate) the capstans, which in turn drive the actuators 70, 72, 74, and 76 of cassette 56. When the actuators 70, 72, 74, and 76 of cassette 56 are engaged with guide wire 58 and working catheter 60, respectively, the actuators 70, 72, 74, and 76 of cassette 56 transfer the rotational movement of the capstans to cause the movement of guide wire 58 and working catheter 60. In another embodiment, the motors that drive the capstans of the motor drive base may be located outside of the base connected to cassette 56 via an appropriate transmission device (e.g., shaft, cable, etc.). In yet another embodiment, cassette 56 includes motors located within cassette 56 associated with the actuators 70, 72, 74, and 76, and cassette 56 is mounted to a base providing a power supply (e.g., battery, AC building power supply, etc.) to the motors within cassette 56.

Figure 3B:
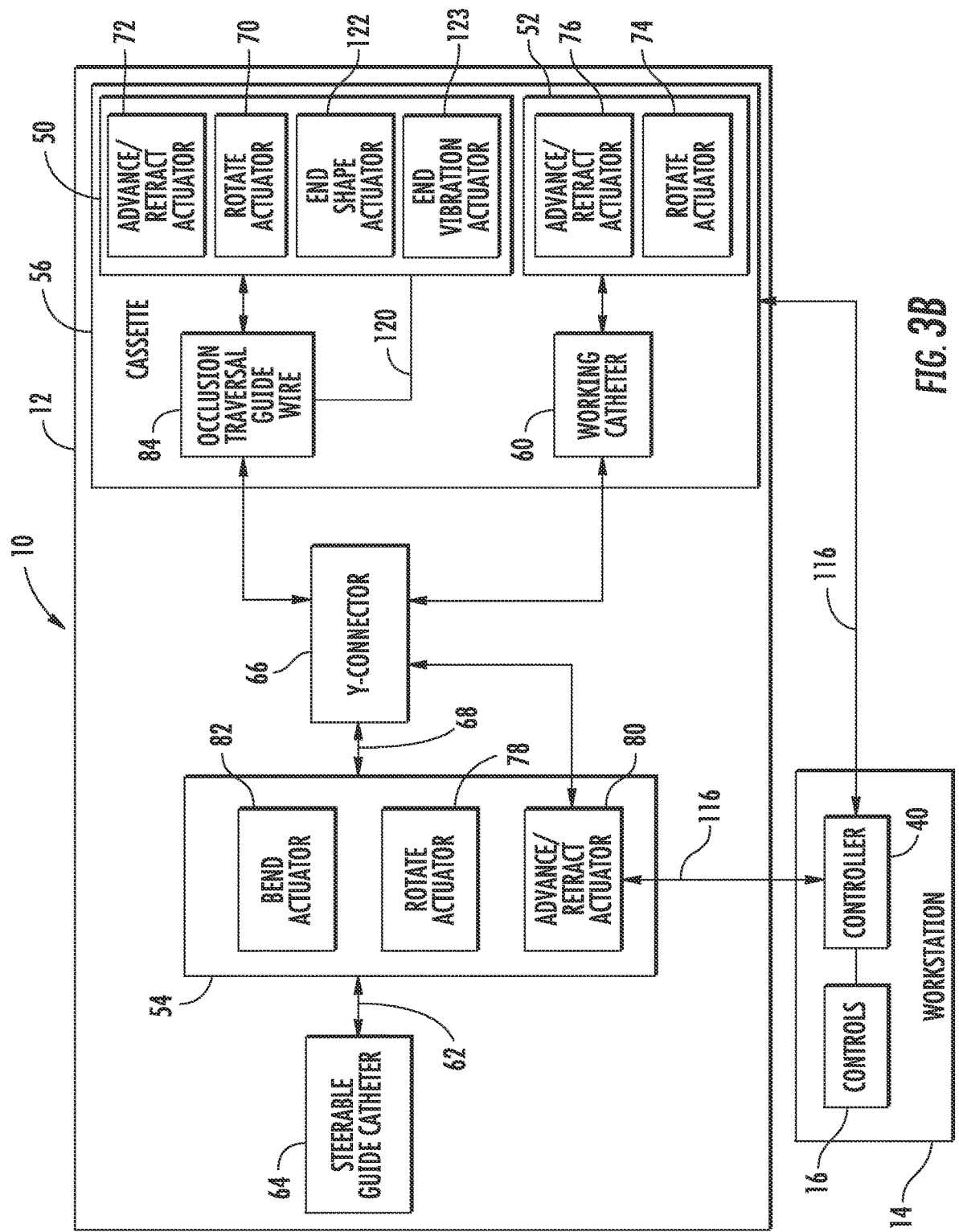
FIG. 3B is a block diagram of a catheter procedure system depicting various actuating mechanisms according to another exemplary embodiment.

Referring to FIG. 3B, a block diagram of catheter procedure system 10 is shown configured for occlusion traversal, according to an exemplary embodiment. Catheter procedure system 10 may be configured for occlusion traversal by loading cassette 56 with an occlusion traversal guide wire 84 in place of guide wire 58. As discussed in more detail below, occlusion traversal guide wire 84 is a guide wire designed or configured to penetrate and traverse (e.g., advance through) a vascular occlusion or a highly stenotic vascular lesion. In one embodiment, occlusion traversal guide wire 84 includes an end section that is structured to create a bore or hole through the lesion as the guide wire 84 is advanced. A working catheter (e.g., a catheter equipped with an angioplasty balloon, stent, etc.) is then able to then be advanced to follow the path or bore through the occlusion created by occlusion traversal guide wire 84 so that the occlusion may be treated using the working catheter.

In one embodiment, when a user intends to use occlusion traversal guide wire 84, occlusion traversal guide wire 84 is coupled to guide wire actuating mechanism 50 in place of guide wire 58. With occlusion traversal guide wire 84 coupled to guide wire actuating mechanism 50, the movement of occlusion traversal guide wire 84 may be controlled by a user via controls 16 and, in some embodiments, may be automatically or semi-automatically controlled by controller 40. As explained in more detail below, in one embodiment, guide wire actuating mechanism 50 includes an actuating mechanism, such as end shape actuator 122, configured to control the shape of the distal end section of occlusion traversal guide wire 84 and a vibration actuator, shown as end vibration actuator 123, configured to cause the distal end section of occlusion traversal guide wire 84 to vibrate. In another embodiment, catheter procedure system 10 may include a separate, dedicated occlusion traversal guide wire actuating mechanism (in addition to guide wire actuating mechanism 50) that is specifically designed to actuate an occlusion traversal guide wire. In one such embodiment, the dedicated occlusion traversal guide wire actuating mechanism and the separate guide wire actuating mechanism 50 may allow the user to control both guide wire 58 and occlusion traversal guide wire 84 without the need to replace one with the other in cassette 56.

Figure 4:
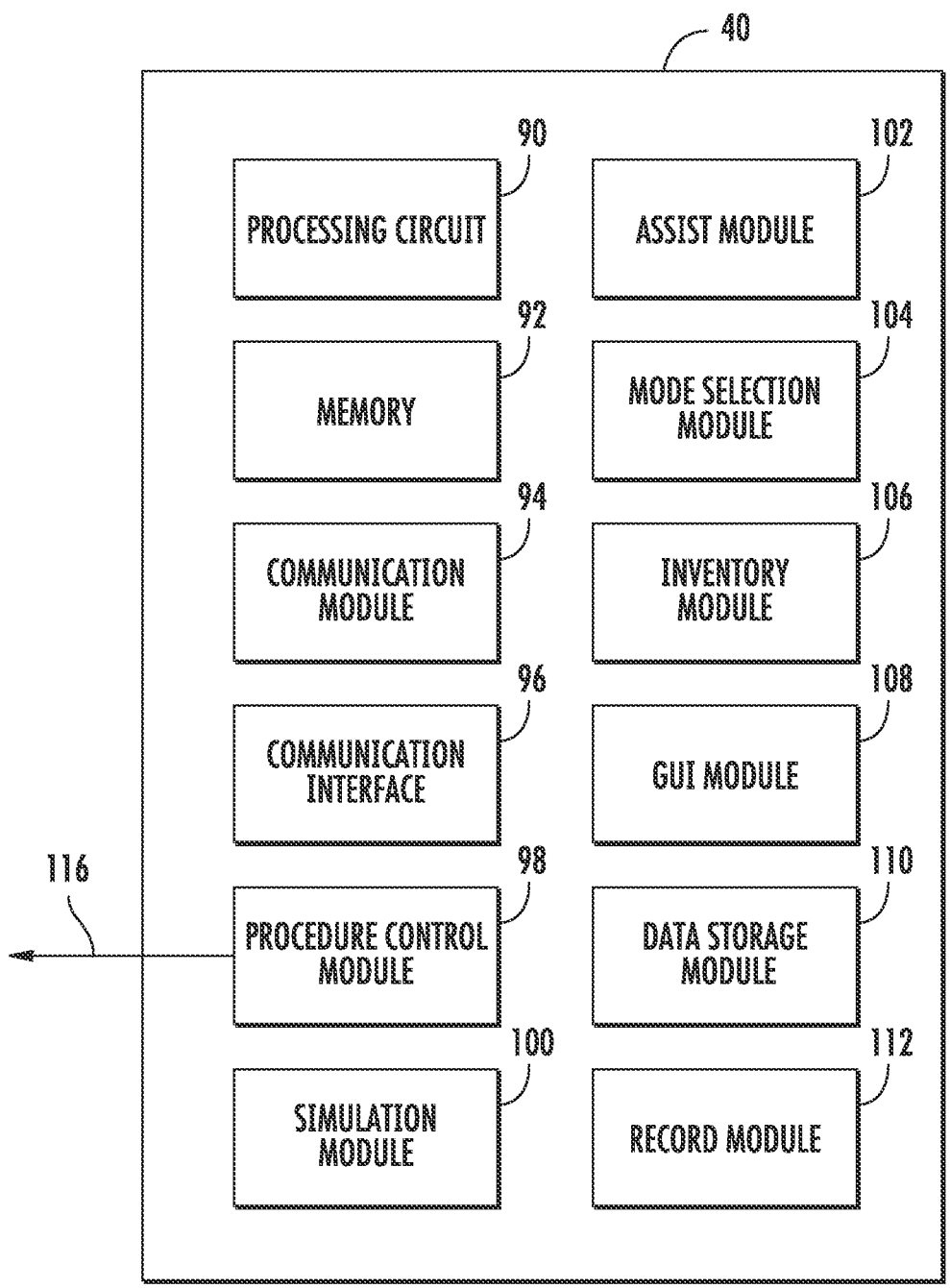
FIG. 4 is a block diagram of a controller for controlling a robotic catheter system according to an exemplary embodiment.

Referring to FIG. 4, a block diagram of a control system, such as controller 40, is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112. In one embodiment, controller 40 may include a movement instruction module that includes one or more instruction sets that dictate how bedside system 12 responds to a user's manipulation of controls 16 to cause a percutaneous device to move in a particular way. The movement instruction module may include various instruction sets to facilitate traversal of a vascular occlusion by the percutaneous devices as discussed herein. Various embodiments of a catheter procedure system 10 including a movement instruction module are disclosed in P.C.T. International Application No. PCT/US2010/52178, filed Oct. 11, 2010, which is incorporated herein by reference in its entirety.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-112. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-112 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-112 may be computer code (e.g., object code, program code, compiled code, script code, executable code, or any combination thereof), hardware, software, or any combination thereof, for conducting each module's respective functions. Module components 94, 98-112 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40.

Controller 40 also includes a procedure control module 98 configured to support the control of bedside system 12 during a catheter based medical procedure. Procedure control module 98 allows the user to operate bedside system 12 by manipulating controls 16. In various embodiments, procedure control module 98 is configured to generate one or more control signals 116 based upon the user's manipulation of controls 16 and/or other data available to procedure control module 98. Referring to FIG. 3A, control signals 116 generated by procedure control module 98 are communicated from controller 40 to the various actuators of bedside system 12. In response to control signals 116, the actuators of cassette 56 cause movement of the guide wire, working catheter and/or guide catheter. Thus, in this manner, the various actuators of bedside system 12 cause movement of various percutaneous device in response to user inputs received by controls 16 and based on other data or control schemes discussed herein. Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

In one embodiment, procedure control module 98 is configured to cause bedside system 12 to move (e.g., advance, retract, rotate, etc.) the percutaneous devices at a set rate in response to a particular input received by controls 16. For example, procedure control module 98 may be configured such that when guide wire control 23 is actuated, bedside system 12 causes the guide wire to advance, retract or rotate at a set rate. In one embodiment, procedure control module 98 may be configured to allow the user to control the rate of movement of a device based on the user's interaction with controls 16. In one embodiment, the movement rate of a percutaneous device caused by bedside system 12 is proportional to the amount of displacement of the control. For example, where controls 23, 25 and 29 are joystick controls, the movement rate of a percutaneous device caused by bedside system 12 is a function of or is proportional to the degree of displacement of the joystick from the resting position.

Controller 40 includes a GUI module 108 the controls the display of various information on the display devices (e.g., monitors 26 and 28, touch screen 18, etc.) of workstation 14. In one embodiment, GUI module 108 is configured to display image data captured by imaging system 32 during a procedure to assist the user of catheter procedure system 10 perform a procedure.

Figure 5:
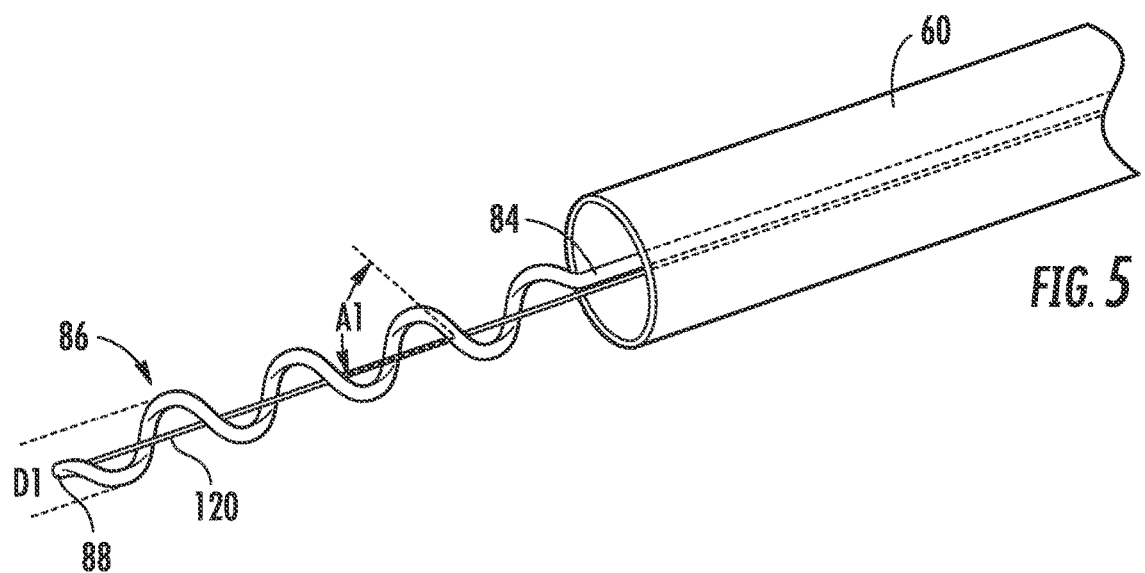
FIG. 5 is a perspective view of an occlusion traversal guide wire and a working catheter according to an exemplary embodiment.

Referring to FIGS. 5-7D, a percutaneous device, such as occlusion traversal guide wire 84, configured to traverse or to create a bore through a vascular lesion is shown according to various exemplary embodiments. Referring to FIG. 5, occlusion traversal guide wire 84 extends through the lumen and out of the distal end of an over-the-wire version of working catheter 60. Occlusion traversal guide wire 84 includes an end section, such as helical end section 86 (e.g., FIG. 5) and end section 230 (e.g., FIG. 7C), that is structured to create a bore through a blockage or lesion located within the vascular system of a patient (e.g., vascular occlusion, a highly stenotic lesion, etc.). Thus, occlusion traversal guide wire 84 is configured to allow occlusion traversal guide wire 84 to penetrate and traverse a vascular lesion. In one such embodiment, helical end section 86 is configured to create a bore through the vascular lesion of sufficient size to allow working catheter 60 to pass through the bore to treat the lesion.

In one embodiment, helical end section 86 is a helical or corkscrew shaped section of the guide wire that terminates in a tip 88 that generally points along the longitudinal axis of occlusion traversal guide wire 84. In one embodiment, tip 88 and end section 86 are more rigid than the rest of guide wire 84. In one such embodiment, tip 88 and helical end section 86 are made from a rigid material suitable for traversing or boring through a vascular occlusion which is a different material than the rest of guide wire 84. In another embodiment, tip 88 and helical end section 86 may be made from the same material as guide wire 84 but are reinforced to provide increased rigidity. To traverse a vascular occlusion, occlusion traversal guide wire 84 may be rotated and advanced to provide a drilling motion as occlusion traversal guide wire 84 is advanced through an occlusion.

In various embodiments, the shape and structure of helical end section 86 may be selected to provide different occlusion traversal properties. In particular, the diameter of the helical section and coil angle may be selected to provide different occlusion traversal properties. For example, referring to FIG. 5, the helical section 86 has a diameter, D1, and a coil angle, A1. In one embodiment, the diameter and/or the coil angle of helical section 86 may be selected or controlled based upon the hardness or level of calcification of the lesion occlusion traversal guide wire 84 is to traverse. For example, a relatively small diameter D1 and/or a relatively small coil angle A1 may be selected to traverse a more solid or calcified lesion or to decrease the amount of pushing force required to be exerted on the wire during occlusion traversal. In other embodiments, a larger diameter D1 and a larger coil angle A1 may be selected to traverse a softer occlusion or to create a larger bore through the occlusion. In one embodiment, the diameter and/or the coil angle of helical section 86 may be selected or controlled based upon the size (e.g., diameter) of the working catheter that will be used to treat the lesion. In one such embodiment, the bore created through the lesion will be of sufficient size to permit passage of the working catheter.

Figure 6:
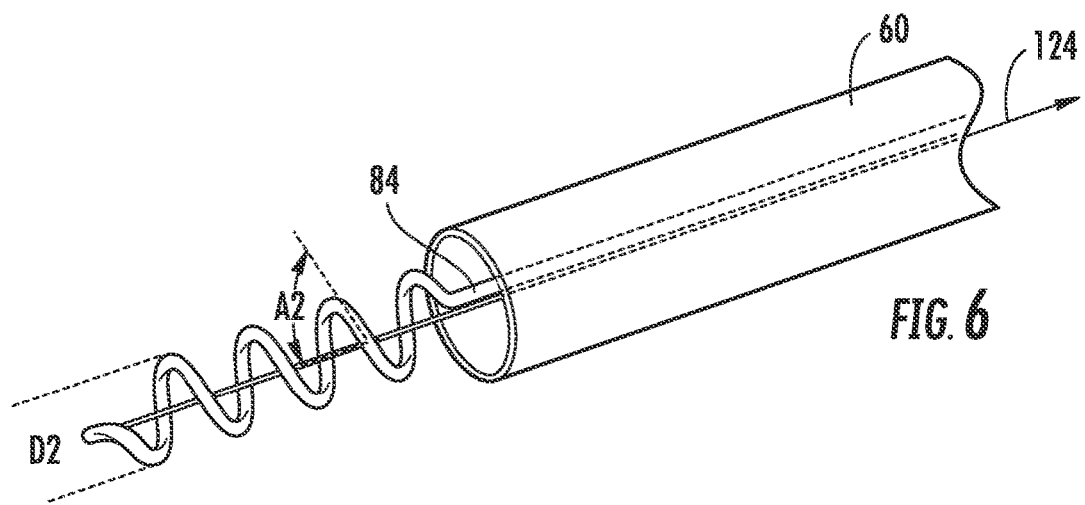
FIG. 6 is a perspective view of the occlusion traversal guide wire and the working catheter of FIG. 5 following a change in shape of the distal portion of the guide wire.

In various embodiments, the shape of helical end section 86 of occlusion traversal guide wire 84 may be changeable, adjustable or controllable to allow the user to vary or control the ability of occlusion traversal guide wire 84 to bore through an occlusion. For example, occlusion traversal guide wire 84 may be configured such that the diameter and the coil angle of helical end section 86 are adjustable or controllable. In one such embodiment, referring to FIG. 5 and FIG. 6, occlusion traversal guide wire 84 includes a control element, such as control wire 120. The distal end of control wire 120 is coupled to tip 88 of occlusion traversal guide wire 84 distal to helical section 86, and the proximal end of control wire 120 is coupled to an actuator, such as end shape actuator 122 in FIG. 3B. Referring to FIG. 6, a force or tension, indicated by arrow 124, is applied to control wire 120 by end shape actuator 122. The tension applied to control wire 120 causes compression of helical section 86 causing both the coil diameter and coil angle of helical section 86 to increase. In other words, with tension applied to control wire 120, D2 is greater than D1 and A2 is greater than A1. Further, the tension applied via control wire 120 also causes the length of helical section 86 to decrease. In one embodiment, working catheter 60 is configured to provide support to the end section of occlusion traversal guide wire 84 such that tension applied to control wire 120 causes compression of helical section 86 instead of retraction of the guide wire. For example, the inner surface of the distal end of working catheter 60 may include a notch or other structure that engages or grasps a portion of guide wire 84 on the proximal side of helical end section 86. In another embodiment, helical end section 86 may be made from a shape-memory alloy, and the shape of helical section 86 may be altered by triggering a shape change in the alloy of helical end section 86. In this embodiment, end shape actuator 122 may include a heating element suitable to trigger the shape change in the shape-memory alloy of helical section 86.

Referring to FIG. 5 and FIG. 6 helical portion 86 includes a plurality of coils all of the coils having a first diameter D1 in a first position and all of the coils having a second diameter D2 larger than the first diameter D1 in a second position.

In various embodiments, the control system, for example controller 40, of catheter procedure system 10 controls the end shape actuator 122 to cause changes in the shape of the end section (e.g., helical end section 86 and end section 230) of occlusion traversal guide wire 84. In one embodiment, catheter procedure system 10 may be configured to allow the user to control the shape of helical section 86 and/or of end section 230 via operation of controls 16.

In one embodiment, the user may input a specific coil diameter and coil angle via controls 16, and controller 40 generates a control signal 116 to control end shape actuator 122 to cause helical section 86 to assume the specific coil diameter and coil angle received via the user input. In one embodiment, controls 16 include a touch screen icon associated with a coil diameter or coil angle that, when activated by the user, causes helical section 86 to assume the shape associated with the icon. In another embodiment, controls 16 may include a control (e.g., a dial, touch screen slide bar, etc.) that allows the user to select the coil diameter or coil angle of helical section 86. In various embodiments, the user may view the progress of occlusion traversal guide wire 84 as it moves through an occlusion via images displayed on monitors 26 or 28, and then adjust the coil diameter and coil angle via controls 16 as needed during traversal.

In another embodiment, procedure control module 98 of controller 40 may be configured to automatically change the coil diameter and coil angle of helical section 86 based upon information accessible to controller 40. In one embodiment, the information may be data related to the performance of a particular procedure. For example, controller 40 may analyze image data to assess how solid a particular occlusion is and based upon the determination of solidity adjust the coil diameter and coil angle of helical section 86 in order to facilitate occlusion traversal. In other embodiments, controller 40 may be configured to monitor the progress of occlusion traversal guide wire 84 through an occlusion and to automatically adjust coil diameter and coil angle of helical section 86 based on the monitored progress. In one exemplary embodiment, bedside system 12 may include one or more sensors to detect the amount of force or resistance experienced by helical section 86 during occlusion traversal, and controller 40 may be configured to control the shape of helical section 86 based upon the detected amount of force. In one such embodiment, the coil diameter and coil angle may be inversely related to the detected force (e.g., coil diameter and coil angle are decreased in response to an increase in detected force). In one embodiment, controller 40 may be configured to automatically decrease coil diameter and coil angle when the amount of force exceeds a threshold and/or may be configured to increase coil diameter and coil angle when the amount of force is below a threshold.

In another embodiment, bedside system 12 may include one or more sensors to detect a movement parameter of helical section 86 (e.g., the speed, acceleration, etc. of helical section 86) during occlusion traversal, and controller 40 may control the shape of helical section 86 based upon the detected movement parameter during occlusion traversal. In one such embodiment, the coil diameter and coil angle may be directly related to the detected speed (e.g., coil diameter and coil angle are increased in response to an increase in the detected speed). In one embodiment, controller 40 may be configured to automatically decrease coil diameter and coil angle when the speed of occlusion traversal guide wire 84 is below a threshold and/or may be configured to increase coil diameter and coil angle when the speed of occlusion traversal guide wire 84 exceeds a threshold. In one embodiment, the sensors that detect the speed of occlusion traversal guide wire 84 are located within cassette 56 and are associated with guide wire actuating mechanism 50 (e.g., encoders, potentiometers, etc.). In another embodiment, controller 40 is configured to determine the speed of occlusion traversal guide wire 84 using image analysis of image data captured by imaging system 32 during occlusion traversal. In one embodiment, controller 40 controls the coil diameter and coil angle via control signals sent to end shape actuator 122 which in turn applies tension to control wire 120 in response to the control signal received from controller 40.

In another embodiment, controller 40 may control the shape of helical section 86 based upon the type (e.g., the size, shape, model, manufacturer, etc.) of working catheter that bedside system 12 is equipped with. For example, controller 40 may be configured to adjust the coil diameter and/or coil angle of helical section 86 to ensure the bore through the lesion is of sufficient size to allow passage through and treatment of the lesion using a particular type of working catheter. Controller 40 may identify the particular type of working catheter being used with bedside system 12 in a variety of ways. In one embodiment, the user selects or inputs the particular type of working catheter being used via controls 16. In one embodiment, the user may select the type of working catheter being used by interacting with a graphical user interface (e.g., a drop down menu). In other embodiments, a bar code on the working catheter is read to allow controller 40 to identify the working catheter. In another embodiment, a radio frequency ID tag associated with the working catheter is read.

Figure 7A:
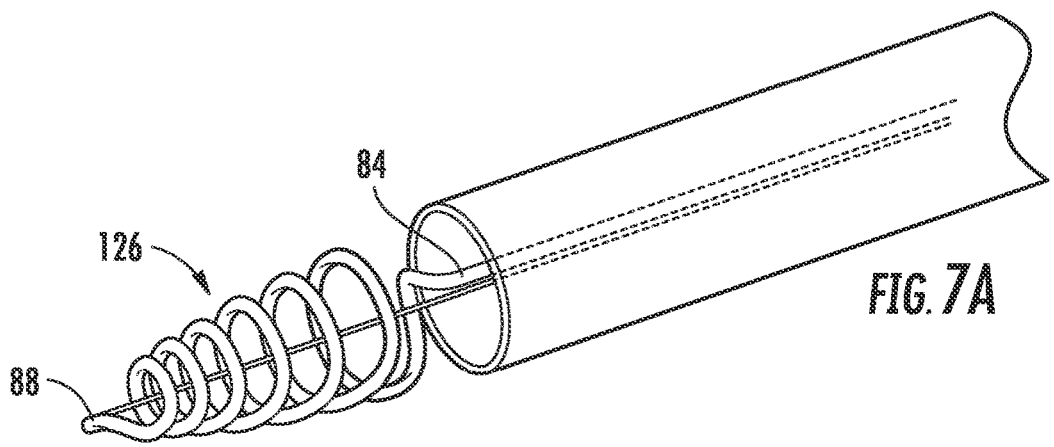
FIG. 7A is a perspective view of an occlusion traversal guide wire and a working catheter according to another exemplary embodiment.

While FIGS. 5 and 6 show a helical section 86 with a constant coil diameter along the length of the helical section, other shapes are possible. For example, referring to FIG. 7A, occlusion traversal guide wire 84 may include a generally cone-shape helical section 126. In this embodiment, the diameter of helical section 126 has a minimum near distal tip 88 and a maximum at the proximal end of helical section 126. As shown, the diameter of helical section 126 decreases along the length of helical section 126 in the proximal to distal direction. While FIGS. 5, 6 and 7A show helical end section 86 as helical section, other configurations and shapes are possible. In one exemplary embodiment, the end section may include one or more cutting edges similar to a drill.

Figure 7B:
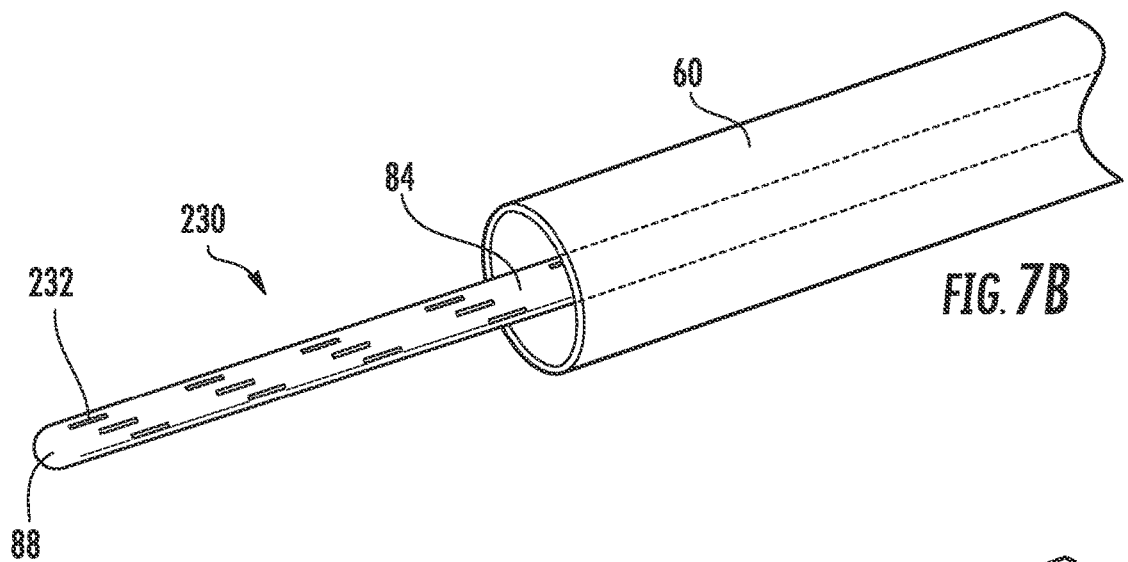
FIG. 7B is a perspective view of an occlusion traversal guide wire and a working catheter according to another exemplary embodiment.
Figure 7C:
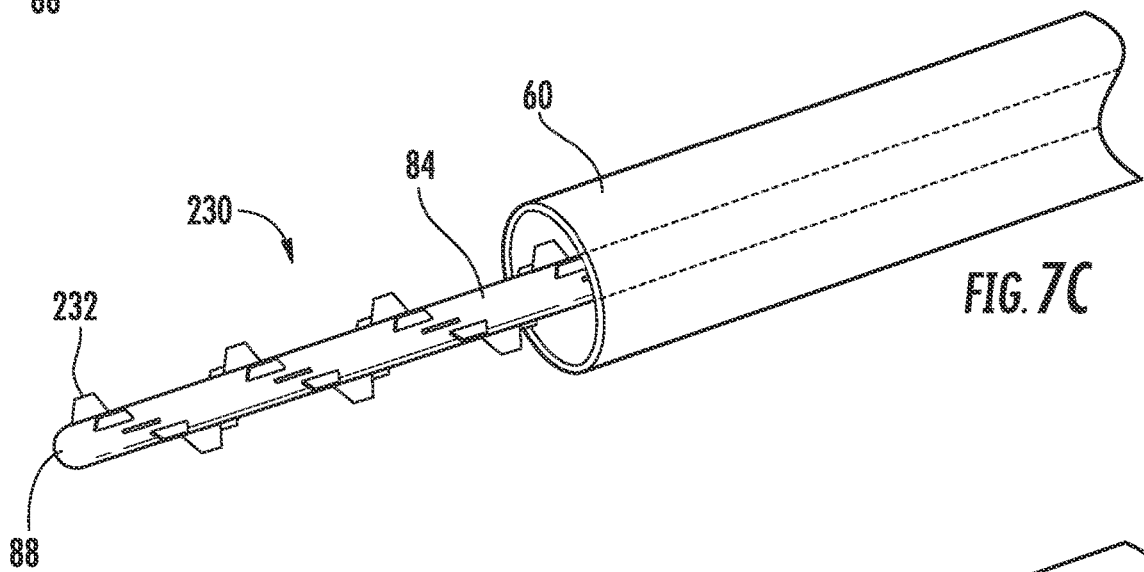
FIG. 7C is a perspective view of the occlusion traversal guide wire and the working catheter of FIG. 7B following a change in shape of the distal portion of the guide wire.
Figure 7D:
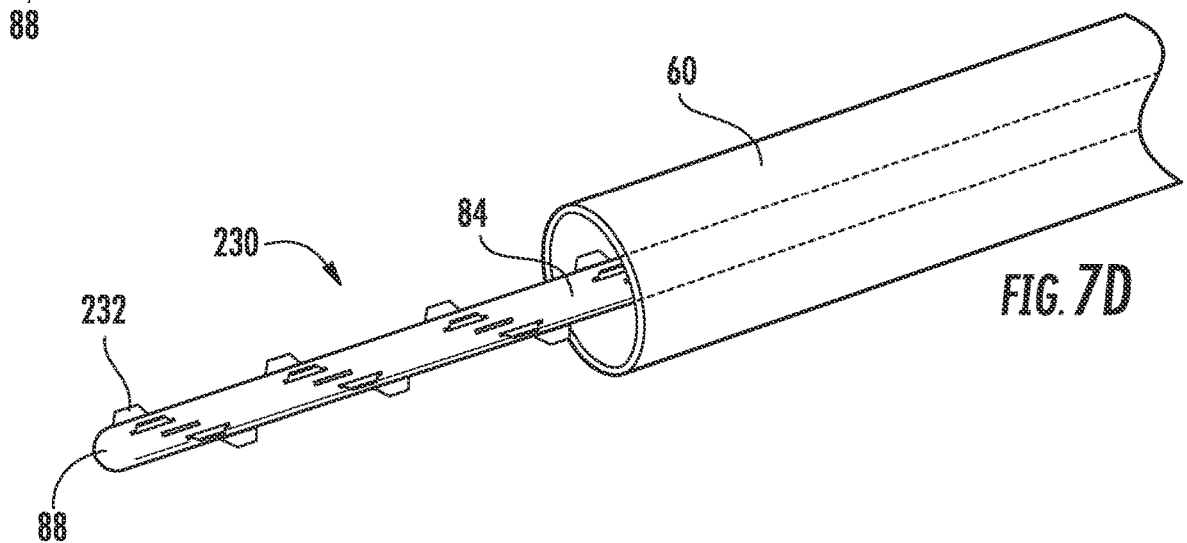
FIG. 7D is a perspective view of the occlusion traversal guide wire and the working catheter of FIG. 7B following a second change in shape of the distal portion of the guide wire.
Figure 8:
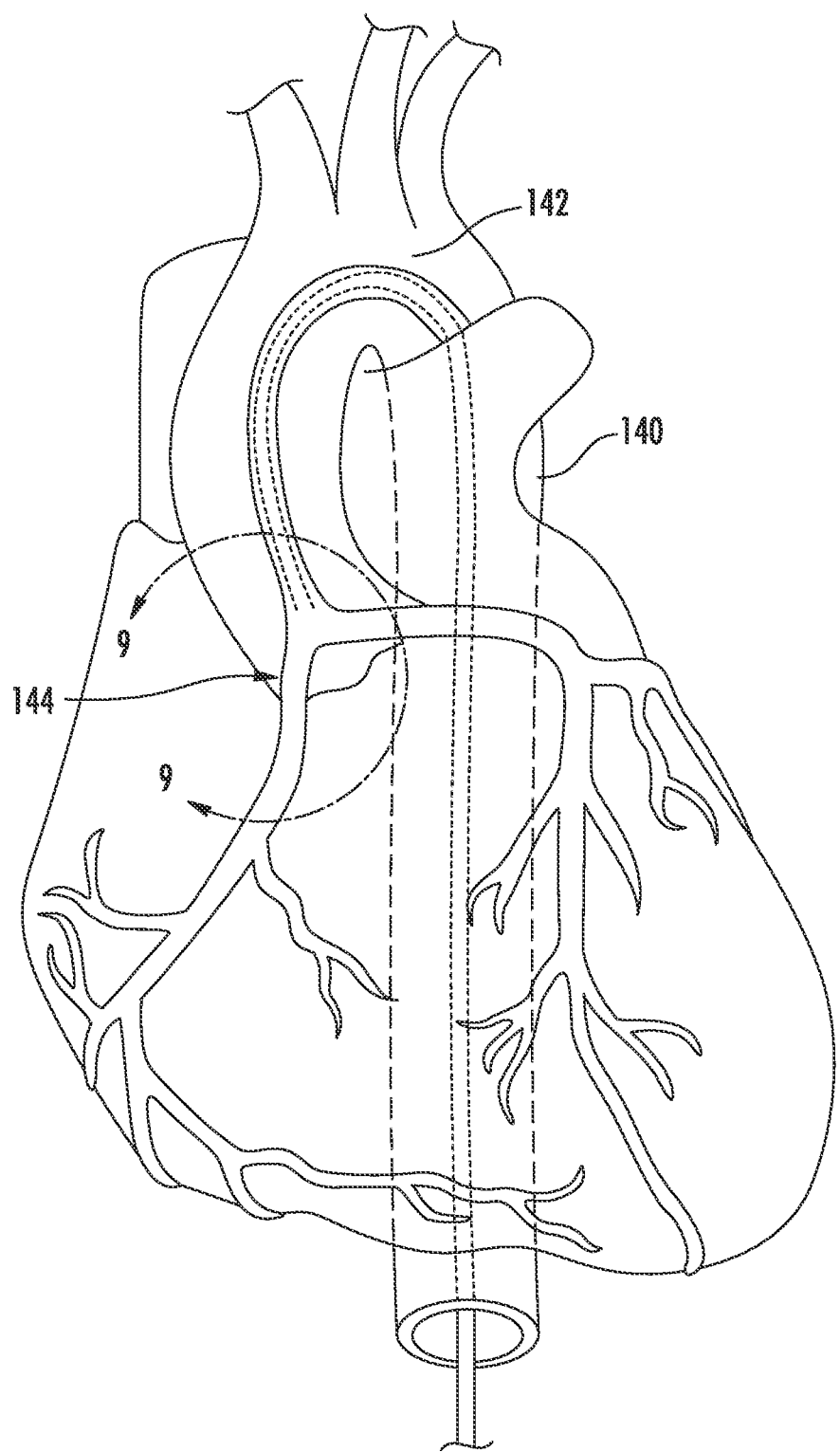
FIG. 8 is an image of a human heart shown during a catheterization procedure according to an exemplary embodiment.

Referring to FIGS. 7B-7D, another embodiment of occlusion traversal guide wire 84 is shown. In this embodiment, occlusion traversal guide wire 84 includes an end section, shown as end section 230, that is structured to create a bore through a blockage or lesion located within the vascular system of a patient. End section 230 includes a plurality of expandable sections (e.g., projections, fins, wings, ridges, etc.), shown as projections 232, which are positioned in a helical pattern around the circumference of guide wire 84. Projections 232 are configured to be moveable between an unexpanded or collapsed position, shown in FIG. 7B, and a fully expanded or extended position, shown in FIG. 7C. Under control of the user, projections 232 are able to expand in the radial direction thereby increasing the radial profile of end section 230. In one embodiment, projections 232 are configured to assume or be placed in a plurality of partially-expanded positions (i.e., positions of expansion between the collapsed position and the fully expanded position) as controlled by the user. For example, FIG. 7D shows projections 232 in a partially extended position approximately half way between collapsed and fully extended.

In this embodiment, occlusion traversal guide wire 84 may include one or more control elements configured to allow the user or procedure control module 98 to control expansion of projections 232. The control element for end section 230 may be coupled to or in communication with an actuator, such as end shape actuator 122 in FIG. 3B. In one embodiment, each projection 232 may be made from a resilient material which is biased toward the expanded position of FIG. 7C, and the control element includes a plurality of control wires, each control wire coupled to one of the projections 232 such that when tension is applied to the control wire associated with a particular the projection 232, the projection is moved toward the collapsed position. In this embodiment, the amount of tension applied to the control wire for each projection is inversely related to the height of the projection. When the control wire is released, the resilient nature of projection 232 results in expansion of the projection.

In one embodiment, to traverse a vascular occlusion, projections 232 may be expanded to the desired size, and guide wire 84 may be rotated and advanced providing a drilling motion as guide wire 84 including end section 230 is advanced through a lesion. In another embodiment, projections 232 may be continuously moved between the collapsed and expanded positions using the radial motion of the expanding projections 232 to compress the material of the lesion and thereby creating a bore through the lesion. In one embodiment, all of projections 232 may be expanded and collapsed together to maximize the compressive force applied to the lesion at any one time. In another embodiment, the projections 232 may be expanded and collapsed at different times in a predetermined pattern to create a bore through the lesion. In one such embodiment, each projection 232 may be expanded and collapsed sequentially, in order, from the distal end to the proximal end of end section 230. In another embodiment, each projection 232 may be expanded and collapsed sequentially, in order, from the proximal end to the distal end of end section 230.

In various embodiments, the shape and structure of end section 230 may be selected to provide different occlusion traversal properties. In particular, the radial dimension and/or the axial dimension of projections 232 may be selected to provide different occlusion traversal properties. In one such embodiment, the maximum radial dimension of projections 232 may be selected in relation to the size of the occlusion that is being traversed. For example, the maximum radial dimension of projections 232 may be directly related to the diameter of the occlusion being traversed such that projection 232 is selected to have a larger radial dimension when guide wire 84 is used to traverse an occlusion with a large diameter.

In various embodiments, procedure control module 98 of controller 40 may be configured to automatically change the expansion size or radial dimension of projections 232 of end section 230 based upon information accessible to controller 40. In one embodiment, the radial dimension of projections 232 may be controlled via the control elements during occlusion traversal based upon the diameter of the occlusion being traversed. In one such embodiment, projections 232 may be controlled to expand based upon the size of the occlusion being traversed. For example, projections 232 may be controlled to expand such that the radial dimension is directly related to the diameter of the occlusion being traversed. In one specific embodiment, the diameter of the occlusion at each position along the length of end section 230 may be determined (e.g., via image processing) and the radial dimension of each projection 232 is controlled separately based upon the measured occlusion diameter adjacent each projection 232. In another embodiment, the pattern or sequence of expansion and contraction of projections 232 may be controlled based upon information related to the occlusion being traversed.

In one embodiment, the user may input a specific expansion size or radial dimension, and controller 40 generates a control signal 116 to control end shape actuator 122 to cause one or more projections 232 to assume the expansion size or radial dimension received via the user input. In one embodiment, controls 16 include a touch screen icon associated with the expansion size that, when activated by the user, causes end section 230 to assume the expansion size associated with the icon. In another embodiment, controls 16 may include a control (e.g., a dial, touch screen slide bar, etc.) that allows the user to select the expansion size of end section 230. In various embodiments, the user may view the progress of occlusion traversal guide wire 84 as it moves through an occlusion via images displayed on monitors 26 or 28, and then adjust the expansion size or radial dimension of projections 232 via controls 16 as needed during traversal.

In another embodiment, bedside system 12 may include one or more sensors to detect a movement parameter of end section 230 (e.g., the speed, acceleration, etc. of end section 230) during occlusion traversal, and controller 40 may control the expansion size of end section 230 based upon the detected movement parameter during occlusion traversal. In one such embodiment, the radial dimension of projections 232 may be directly related to the detected speed (e.g., the radial dimension of projections 232 is increased in response to an increase in the detected speed). In one embodiment, controller 40 may be configured to automatically decrease the radial dimension of projections 232 when the speed of occlusion traversal guide wire 84 is below a threshold and/or may be configured to increase the radial dimension of projections 232 when the speed of occlusion traversal guide wire 84 exceeds a threshold. In one embodiment, the sensors that detect the speed of occlusion traversal guide wire 84 are located within cassette 56 and are associated with guide wire actuating mechanism 50 (e.g., encoders, potentiometers, etc.). In another embodiment, controller 40 is configured to determine the speed of occlusion traversal guide wire 84 using image analysis of image data captured by imaging system 32 during occlusion traversal. In one embodiment, controller 40 controls the radial dimension of projections 232 via control signals sent to end shape actuator 122 which in turn applies tension to control elements in response to the control signal received from controller 40.

In another embodiment, controller 40 may control the shape of end section 230 based upon the type (e.g., the size, shape, model, manufacturer, etc.) of working catheter that bedside system 12 is equipped with. For example, controller 40 may be configured to adjust the radial dimension of projections 232 to ensure the bore through the lesion is of sufficient size to allow passage through and treatment of the lesion using a particular type of working catheter. Controller 40 may identify the particular type of working catheter being used with bedside system 12 in a variety of ways. In one embodiment, the user selects or inputs the particular type of working catheter being used via controls 16. In one embodiment, the user may select the type of working catheter being used by interacting with a graphical user interface (e.g., a drop down menu). In other embodiments, a bar code on the working catheter is read to allow controller 40 to identify the working catheter. In another embodiment, a radio frequency ID tag associated with the working catheter is read.

Referring to FIGS. 8-12, an exemplary balloon angioplasty therapeutic procedure is shown utilizing occlusion traversal guide wire 84 including helical end section 86. During the exemplary procedure shown, an incision is made, usually in the groin. A guide catheter 64 is inserted through the incision into the femoral artery. Bedside system 12 is operated via controls 16 and controller 40 to feed guide catheter 64 through the patient's aorta 140 over the aortic arch 142 until guide catheter 64 is positioned near either the left or right ostium leading into the patient's coronary arteries 144. In another embodiment, guide catheter 64 may be manually positioned within a patient's vascular system.

Figure 9:
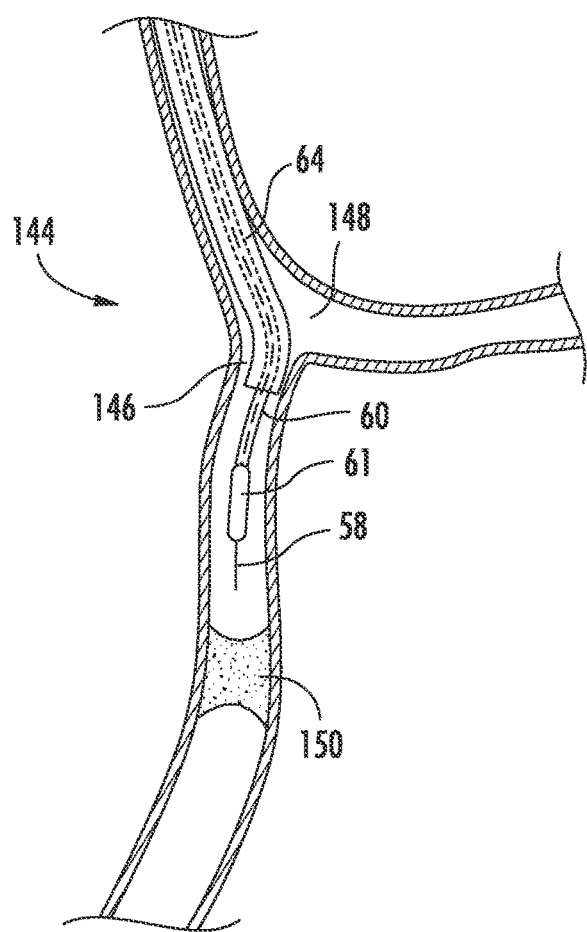
FIG. 9 is an image of the coronary arteries shown during a catheterization procedure according to an exemplary embodiment.

Referring to FIG. 9, guide catheter 64 may be positioned such that the distal opening of guide catheter 64 provides access to either left ostium 146 or right ostium 148 (access to left ostium 146 is shown in FIG. 9). In one embodiment, guide catheter 64 is a steerable guide catheter such that the distal end of guide catheter 64 may be bent via bend actuator 82 (e.g., FIG. 3A) to position the distal end of guide catheter 64 within the ostium as desired by the user. With the guide catheter positioned within the ostium, bedside system 12 is then operated via controls 16 and controller 40 to feed guide wire 58 through guide catheter 64 until guide wire 58 extends from the distal end of guide catheter 64 adjacent the total occlusion lesion 150. Next, bedside system 12 is operated via controls 16 and controller 40 to advance working catheter 60 through guide catheter 64 over guide wire 58 such that the distal end of working catheter 60 and angioplasty balloon 61 are adjacent lesion 150.

Figure 10:
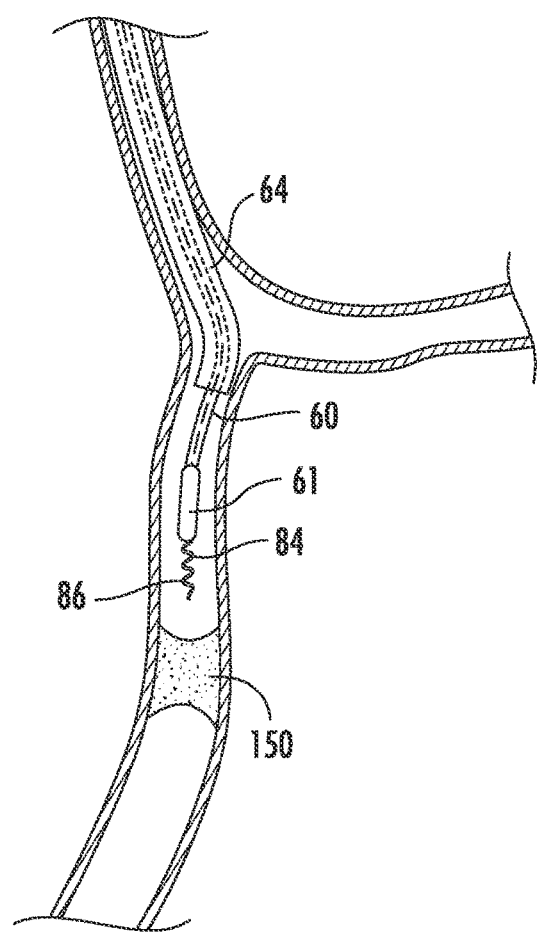
FIG. 10 is an image of the coronary arteries of FIG. 9 showing an occlusion traversal guide wire prior to traversal of a lesion according to an exemplary embodiment.

Referring to FIG. 10, with working catheter 60 and balloon 61 in place adjacent lesion 150, bedside system 12 is operated via controls 16 and controller 40 to retract guide wire 58 out of the proximal end of both working catheter 60 and guide catheter 64. During retraction of guide wire 58, both working catheter 60 and guide catheter 64 are held in place within the coronary arteries. Guide wire 58 is removed from guide wire actuating mechanism 50, and occlusion traversal guide wire 84 is coupled to guide wire actuating mechanism 50 in place of guide wire 58. In one embodiment, guide wire actuating mechanism 50 may include one or more pairs of engagement wheels, and guide wire actuating mechanism 50 is coupled to guide wire actuating mechanism 50 via engagement of the engagement wheels with the outer surface of guide wire 84. Bedside system 12 is operated via controls 16 and controller 40 to advance occlusion traversal guide wire 84 through the lumen of working catheter 60 such that the end section (e.g., helical end section 86, cone-shape helical section 126, end section 230, etc.) of occlusion traversal guide wire 84 extends from the distal end of working catheter 60. In this position, the end section of occlusion traversal guide wire 84 is positioned adjacent to lesion 150.

Figure 11:
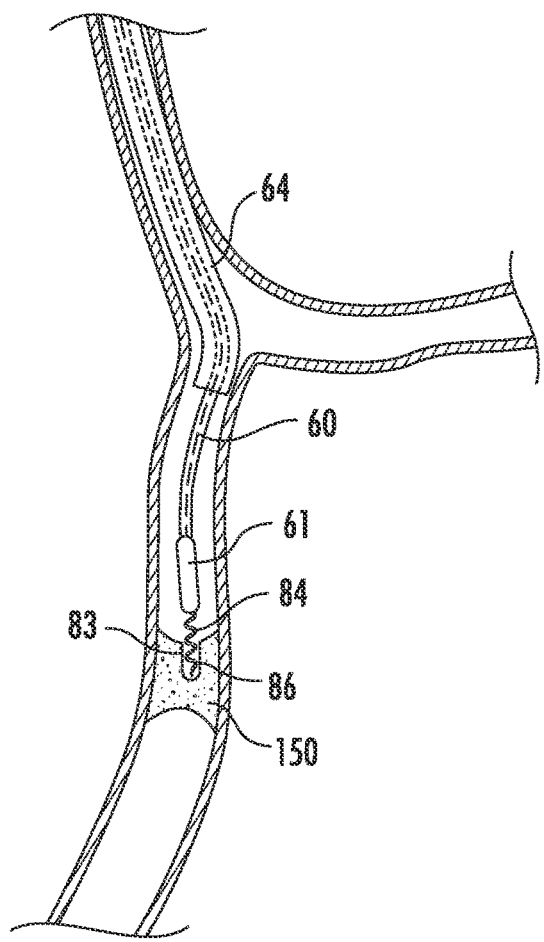
FIG. 11 is an image of the coronary arteries of FIG. 9 showing an occlusion traversal guide wire during traversal of a lesion according to an exemplary embodiment.

Referring to FIG. 11, to begin occlusion traversal, the appropriate actuator of bedside system 12 is operated via controls 16 and controller 40 to advance occlusion traversal guide wire 84 such that the end section of occlusion traversal guide wire 84 begins to pass into lesion 150. Occlusion traversal guide wire 84 may be rotated continuously as the guide wire is advanced such that the end section of occlusion traversal guide wire 84 provides a drilling motion to facilitate occlusion traversal and to create a bore 83 through the lesion. In another embodiment, occlusion traversal guide wire 84 may be rotated continuously during either advancement or retraction, providing a drilling motion during both advancement and retraction. In various embodiments, an anti-embolic device may be used in conjunction with occlusion traversal guide wire 84 to trap or catch pieces of lesion 150 that may become dislodged during creation of bore 83.

In various embodiments, the shape or size of the end section (e.g., helical end section 86, cone-shape helical section 126, end section 230, etc.) of occlusion traversal guide wire 84 may be controlled, either by the user or automatically as discussed above, to facilitate occlusion traversal. For example, in one embodiment, helical end section 86 may be controlled to increase its diameter while helical end section 86 is located within lesion 150 resulting in a compression of the material of lesion 150. In another embodiment, end section 230 may be controlled to expand projections 232 while end section 230 is located within lesion 150 resulting in a compression of the material of lesion 150. In one embodiment, working catheter 60 is advanced by bedside system 12 as occlusion traversal guide wire 84 is advanced such that the position of working catheter 60 relative to occlusion traversal guide wire 84 remains substantially constant.

Figure 12:
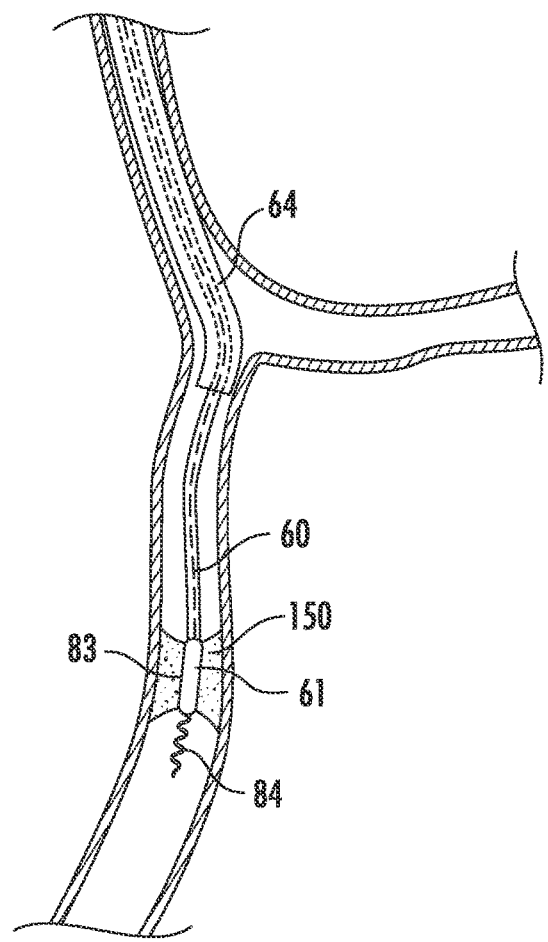
FIG. 12 is an image of the coronary arteries of FIG. 9 showing an occlusion traversal guide wire following traversal of a lesion according to an exemplary embodiment.

Referring to FIG. 12, occlusion traversal guide wire 84 is advanced in the drilling motion creating bore 83 that extends through the total occlusion lesion 150, and working catheter 60 is advanced through the bore created by occlusion traversal guide wire 84. In one embodiment, occlusion traversal guide wire 84 is configured to make a bore through lesion 150 that is large enough to permit passage of working catheter 60 and balloon 61. In one embodiment, guide wire 84 passes substantially along the center axis of lesion 150. Occlusion traversal guide wire 84 is advanced until lesion 150 is completely traversed, and working catheter 60 is advanced until balloon 61 is positioned across lesion 150. Because working catheter 60 follows guide wire 84 through the bore created by guide wire 84, balloon 61 is also positioned substantially along the center axis of lesion 150 and/or the center axis of the blood vessel. Once working catheter 60 and balloon 61 are in place, balloon 61 is inflated to compress lesion 150 and to stretch the artery open thereby increasing blood flow to the heart. Balloon 61 is then deflated, occlusion traversal guide wire 84, working catheter 60 and guide catheter 64 are retracted and removed from the patient, and the incision is closed. It should be understood that while, FIGS. 8-12 show an exemplary procedure using occlusion traversal guide wire 84 having a helical end section 86, in other embodiments, the exemplary procedure discussed above may be preformed using an occlusion traversal guide wire 84 having a different end section (e.g., cone-shape helical section 126, end section 230, etc.).

As noted above, bedside system 12 may include an actuator (shown as end vibration actuator 123 in FIG. 3B) configured to generate a vibration that is transmitted through the length of occlusion traversal guide wire 84 to cause at least a portion of the end section of the guide wire to vibrate. The vibration of the end section of occlusion traversal guide wire 84 may facilitate occlusion traversal by causing compression of the material of lesion. Further, vibration of the end section of occlusion traversal guide wire 84 may facilitate advancement and retraction of the guide wire through the occlusion. For example, vibration of the end section of occlusion traversal guide wire 84 may act to dislodge guide wire 84 from lesion 150 in the event that the guide wire becomes stuck within lesion.

End vibration actuator 123 may be configured to generate various types of vibration. End vibration actuator 123 may be configured to generate vibration of different frequencies. In one embodiment, end vibration actuator 123 may be configured to generate ultrasonic vibration that breaks up the material of lesion 150. In various embodiments, controls 16 may include a user input (e.g., a touch screen icon) associated with a particular vibration frequency and actuation of the user input causes controller 40 to generate a control signal to end vibration actuator 123 triggering vibration of the end section of occlusion traversal guide wire 84 at the selected frequency. In another embodiment, procedure control module 98 may be configured to automatically cause vibration of the end section of occlusion traversal guide wire 84 based upon the degree of calcification of lesion 150 to improve or optimize the breakup of lesion 150 caused by the vibration. In one such embodiment, the degree of calcification of lesion 150 may be determined via image processing of image date of lesion 150.

End vibration actuator 123 may be configured to cause occlusion traversal guide wire 84 to vibrate in a variety of directions. In one embodiment, end vibration actuator 123 may be configured to cause occlusion traversal guide wire 84 to vibrate in the axial direction. In another embodiment, end vibration actuator 123 may be configured to cause occlusion traversal guide wire 84 to vibrate in the radial direction (i.e., substantially perpendicular to the axis of the guide wire). In other embodiments, end vibration actuator 123 may be configured to cause occlusion traversal guide wire 84 to vibrate in both the axial and the radial direction.

End vibration actuator 123 and/or the end section of occlusion traversal guide wire 84 may be configured such that select portions of the end section of the guide wire vibrate. In one embodiment, only tip 88 of occlusion traversal guide wire 84 vibrates. In other embodiments, the whole end section of occlusion traversal guide wire 84 vibrates. In one specific embodiment, end vibration actuator 123 and/or end section 230 may be configured such that projections 232 vibrate while the rest of end section 230 remains substantially still.

In the embodiment shown if FIG. 3B, guide wire actuating mechanism 50 includes a separate end vibration actuator 123. In one such embodiment, the vibration generated by end vibration actuator 123 may be transmitted to the guide wire through the engagement structure of advance/retract actuator 72 and/or rotate actuator 70. In other embodiments, one of the other actuators of guide wire actuating mechanism 50 may be configured to generate the vibration of the end section of occlusion traversal guide wire 84. In one such embodiment, advance/retract actuator 72 may be configured to generate vibration by triggering small amounts of advancement and retraction. In one embodiment, advance/retract actuator 72 may include a plurality of wheels that engage the guide wire to impart motion to the guide wire, and the vibration is transmitted to the guide wire through the wheels.

In various exemplary embodiments, the direction or heading of occlusion traversal guide wire 84 may be controlled such that the path created by occlusion traversal guide wire 84 is in the proper location and/or to ensure that occlusion traversal guide wire 84 exits the lesion 150 at the intended location. In one embodiment, the direction or heading of occlusion traversal guide wire 84 may be controlled via rotation of occlusion traversal guide wire 84. Tip 88 may include a permanent bend such that tip 88 points at an angle relative to the longitudinal axis of guide wire 84. To control its direction, occlusion traversal guide wire 84 may be rotated such that bent tip 88 is pointing in the intended direction of travel, and then occlusion traversal guide wire 84 is advanced such that bent tip 88 engages lesion 150 and is advanced creating a bore in the direction of bent tip 88. Thus, by rotating occlusion guide wire 84 prior to entry into lesion 150, the user may select the path that occlusion guide wire 84 will take during occlusion traversal.

As discussed above, the user may view the progress of occlusion traversal guide wire 84 as it moves through lesion 150 via images displayed on monitors 26 or 28. By viewing occlusion traversal guide wire 84 during occlusion traversal, the user may assess whether occlusion traversal guide wire 84 is advancing along the desired path through lesion 150. If the user wishes to advance occlusion traversal guide wire 84 along a different path, the user may retract occlusion traversal guide wire 84 from lesion 150, rotate occlusion traversal guide wire 84 such that the bent tip 88 is pointing in the desired direction, and then advance occlusion traversal guide wire 84 in the new direction through lesion 150. The user may change the direction of occlusion traversal guide wire 84 for a variety of reasons. For example, the direction may be changed to ensure the bore through lesion 150 is in the proper position for treatment of the lesion via working catheter 60 or to ensure that occlusion traversal guide wire 84 does not contact the wall of the artery upon exit from lesion 150.

In various embodiments, occlusion traversal guide wire 84 may be a steerable guide wire. In such embodiments, the shape of the end section (e.g., helical end section 86, cone-shape helical section 126, end section 230, etc.) of occlusion traversal guide wire 84 and/or tip 88 may be altered to steer occlusion traversal guide wire 84. For example, in one embodiment, control wire 120 may be coupled to tip 88 such that when tension is applied to control wire 120, tip 88 bends away from the longitudinal axis of the guide wire. With tip 88 bent away from the longitudinal axis, occlusion traversal guide wire 84 is advanced along a path in the direction of bent tip 88. Thus, in these embodiments, the user may actively control or alter the direction of occlusion traversal guide wire 84 during traversal of lesion 150 without requiring the user to withdraw the guide wire from lesion 150. This may allow the user to more precisely control steering of occlusion traversal guide wire 84 through a lesion located in a curved section of artery or in changing the path of occlusion traversal guide wire 84 to avoid contact with the wall of the artery upon exit from lesion 150.

In various embodiments, the user may view images of coronary arteries 144 captured by imaging system 32 to facilitate the user's treatment of lesion 150 as discussed above regarding FIGS. 8-12. In particular, the user may view the progress of occlusion traversal guide wire 84 as it moves through lesion 150 via images displayed on monitors 26 or 28. In one embodiment, the angular position of imaging system 32 relative to the patient may be controlled to obtain and display various angular views of the patient's heart or coronary arteries 144 on first monitor 26 and/or second monitor 28. Displaying different angular views at different portions of the procedure may aid the user of workstation 14 to properly move or steer occlusion traversal guide wire 84 through lesion 150. In one embodiment, controls 16 may be operated by the user to control the angular position of imaging system 32.

While the catheter based therapeutic procedure discussed above relates to a balloon angioplasty, it should be understood that the working catheter may be any type of catheter useful during the performance of any therapeutic procedure. For example, the catheter may include a stent that is expanded and left at the site of the lesion. Alternatively, the working catheter may include structures adapted to cut or grind away the plaque forming the lesion.

In various embodiments, procedure control module 98 is configured to support the control of working catheter 60, guide catheter 64 and occlusion traversal guide wire 84 by bedside system 12 during an occlusion traversal procedure. In some embodiments, procedure control module 98 is configured to provide semi-automated control of one or more of the percutaneous devices of bedside system 12. Semi-automated control provided by procedure control module 98 may simplify the control of one or more percutaneous devices, including occlusion traversal guide wire 84, by allowing the user to control relatively complex actions or movements via relatively simple operation of controls 16.

In one such embodiment, procedure control module 98 is configured to control the relative movement between two or more percutaneous devices during an occlusion traversal procedure. For example, procedure control module 98 may be configured to control movement of both occlusion traversal guide wire 84 and working catheter 60 such that the relative motion between the percutaneous devices during occlusion traversal is substantially zero (i.e., both guide wire 84 and working catheter 60 advance and retract during occlusion traversal at the same rate). In one such embodiment, during occlusion traversal, the user may operate a single input of controls 16 (e.g., dedicated guide wire control joystick 23) to cause occlusion traversal guide wire 84 to advance through a lesion, and procedure control module 98 may be configured to automatically cause working catheter 60 to advance at the same rate as occlusion traversal guide wire 84 without requiring the user to also operate controls 16 (e.g., dedicated working catheter control joystick 25) to cause advancement of working catheter 60. This ensures that balloon 61 of working catheter 60 remains at a set distance behind the tip of occlusion traversal guide wire 84 during occlusion traversal, and it also simplifies performance of the occlusion traversal procedure by providing movement of both guide wire 84 and working catheter 60 based on the user's operation of a single control. In another embodiment, the user may operate dedicated working catheter control 25, and procedure control module 98 is configured to cause automatic advancement of guide wire 84 to ensure the relative position of working catheter 60 and guide wire 84 is maintained during the occlusion traversal procedure. In addition, procedure control module 98 may be configured to control the motion of guide catheter 64 relative to occlusion traversal guide wire 84.

In various embodiments, procedure control module 98 may be configured to allow a user to select or define the desired relative movement between one or more percutaneous devices. For example, procedure control module 98 may be configured to allow the user to select, via an input received by controls 16, various rates of relative movement between occlusion traversal guide wire 84 and working catheter 60. In one such embodiment, procedure control module 98 is configured to automatically cause working catheter 60 to move as the user controls movement of occlusion traversal guide wire 84 to maintain the selected relative rate of movement.

In other semi-automated embodiments, procedure control module 98 may be configured to cause bedside system 12 to rotate occlusion traversal guide wire 84 at a set rate as the guide wire is advanced and/or retracted by the user's operation of controls 16. In such an embodiment, procedure control module 98 may specify an amount of rotation experienced by occlusion traversal guide wire 84 as it is advanced or retracted (i.e., a rotation rate). The rotation rate may be specified in terms of degrees of rotation per unit of axial distance traveled (e.g., 360 degrees of rotation for each 2 mm traveled, etc.) or may be specified in terms of degrees of rotation per unit of time of axial travel (e.g., 360 degrees of rotation for each 5 seconds of axial travel). This embodiment allows the user to perform a drilling or corkscrew action with occlusion traversal guide wire 84 without having to manually operate controls 16 to cause both axial movement and rotation. In one such embodiment, during occlusion traversal, the user may operate a single input of controls 16 (e.g., dedicated guide wire control joystick 23) to cause occlusion traversal guide wire 84 to advance through a lesion, and procedure control module 98 may be configured to automatically cause rotation of occlusion traversal guide wire 84 during advancement with without requiring the user to specifically operate controls 16 to cause rotation of occlusion traversal guide wire 84. In various embodiments, procedure control module 98 is configured to allow the user to set, select or define via an input received by controls 16 the desired rotation rate. In various embodiments, procedure control module 98 may be configured to allow the user to adjust the rotation rate via an input received by controls 16 (e.g., a touch screen icon) during a procedure.

In another embodiment, procedure control module 98 may be configured to cause bedside system 12 to advance and/or retract occlusion traversal guide wire 84 at a set rate in response to the user's operation of controls 16. For example, controls 16 may include a control (e.g., a touch screen icon) that allows the user to toggle on advancement of occlusion traversal guide wire 84. When the control is toggled to the on position, procedure control module 98 is configured to cause occlusion traversal guide wire 84 to advance at the specified rate until the control is toggled off. In various embodiments, procedure control module 98 is configured to allow the user to set, select or define via an input received by controls 16 the desired advancement and/or retract rate of occlusion traversal guide wire 84.

In other embodiments, procedure control module 98 may be configured to operate in a fully manual mode to allow the user to specifically control all of the movements of one or more percutaneous devices via controls 16. In one exemplary embodiment, procedure control module 98 is configured to allow the user to specifically control all movement (including advancement, retraction and rotation) of occlusion traversal guide wire 84 via operation controls 16, and, in one specific embodiment, via operation of dedicated guide wire control joystick 23. In various embodiments, procedure control module 98 may be configured to allow the user to switch between full manual control of occlusion traversal guide wire 84 and one or more of the semi-automated control schemes discussed above. In one such embodiment, controls 16 include a control (e.g., a touch screen icon) that, when activated, switches procedure control module between semi-automated mode and fully manual mode.

As noted above, catheter procedure system 10 may include a variety of additional systems that may be used during a catheterization procedure. For example, referring to FIG. 2, catheter procedure system 10 may include a contrast media injection system 13, a medicine/drug injection system 15 and/or an ablation system 17. In such embodiments, procedure control module 98 may be configured to facilitate control of the additional systems during occlusion traversal.

In various embodiments, controller 40 controls the contrast media injection system 13, the medicine/drug injection system 15 and/or the ablation system 17 based upon progress of the first percutaneous device through the lesion. In one embodiment, procedure control module 98 is configured to control contrast media injection system 13 at appropriate times during occlusion traversal. Control of contrast media injection in this manner may facilitate imaging of the lesion during the procedure. In one embodiment, procedure control module 98 is configured to automatically cause the injection of contrast media at various stages of occlusion traversal. For example, contrast media may be automatically injected at the beginning of occlusion traversal (e.g., when the tip of guide wire 84 enters occlusion 150), midway through occlusion traversal (e.g., when the tip of guide wire 84 is at the midpoint of lesion 150) and at the end of occlusion traversal (e.g., when the tip of guide wire 84 exits occlusion 150). In another embodiment, procedure control module 98 may be configured to periodically inject contrast media during occlusion traversal (e.g., contrast media may be injected every several seconds during occlusion traversal). In one embodiment, procedure control module 98 may be configured to allow the user to select or define via controls 16 when contrast media is injected during occlusion traversal. In various embodiments, procedure control module 98 may also be configured to automatically cause imaging system 32 to capture an image of the patient's heart each time contrast media is injected.

Procedure control module 98 may also be configured to control drug injection system 15 at appropriate times during occlusion traversal. In various embodiments, procedure control module 98 may be configured to automatically inject a drug at various stages of occlusion traversal by guide wire 84, at various time points during occlusion traversal and/or periodically during occlusion traversal. In one embodiment, procedure control module 98 may be configured to allow the user to select or define via controls 16 when drug is injected during occlusion traversal.

Procedure control module 98 may also be configured to control an ablation system 17 to trigger ablation of lesion 150 and/or surrounding tissue at appropriate times during occlusion traversal. Ablation system 17 may be any ablation system of past, present or future. In one embodiment, ablation system 17 may be a radiofrequency ablation device incorporated into occlusion traversal guide wire 84. In another embodiment, ablation system 17 may be a cryoablation system incorporated into occlusion traversal guide wire 84. In one embodiment, procedure control module 98 may be configured to allow the user to select or define via controls 16 when ablation system 17 is triggered during a procedure.

As discussed above regarding FIG. 4, controller 40 includes an assist module 102. Generally, assist module 102 is configured to provide information to the user located at workstation 14 to assist the user with the performance of a procedure. In various embodiments, assist module 102 may be configured to provide information to the user located at workstation 14 to assist the user in traversal of lesion 150 using occlusion traversal guide wire 84. For example, an image of coronary arteries 144 and lesion 150 may be displayed on monitors 26 or 28, and assist module 102 may be configured to cause the display of a graphic (e.g., a highlighted line) representative of a suggested path through lesion 150 that occlusion traversal guide wire 84 should follow. The user then may operate controls 16 to cause occlusion traversal guide wire 84 to follow the path displayed by assist module 102.

Assist module 102 may be configured to generate or determine the suggested path based upon data related to the lesion to be treated and/or the blood vessel containing lesion 150. In one embodiment, the suggested path may be displayed along the central axis of either lesion 150 or of the blood vessel, and assist module 102 may determine the central axis via image analysis of images of lesion 150 or of coronary arteries 144 captured by imaging system 32. In another embodiment, assist module 102 may generate the suggested path to ensure that occlusion traversal guide wire 84 will not contact the wall of the artery after exiting from lesion 150.

In another embodiment, assist module 102 may be configured to cause the display of a graphic of a projected path through lesion 150. In this embodiment, assist module 102 may determine the projected path based upon various movement parameters of occlusion traversal guide wire 84 (e.g., current position, direction, velocity, acceleration, etc.) during traversal of lesion 150. The projected path indicates the anticipated or projected positions of occlusion traversal guide wire 84 if occlusion traversal guide wire 84 continues on the current path. In one embodiment, the projected path displayed by assist module 102 may assist the user identify the point that occlusion traversal guide wire 84 will exit lesion 150. If the exit point of occlusion traversal guide wire 84 is too close to the wall of the artery, the user may operate controls 16 to change the path of occlusion traversal guide wire 84, as discussed above, such that occlusion traversal guide wire 84 exits lesion 150 at a position to limit the chance that occlusion traversal guide wire 84 may contact the wall of the artery.

Figure 13:
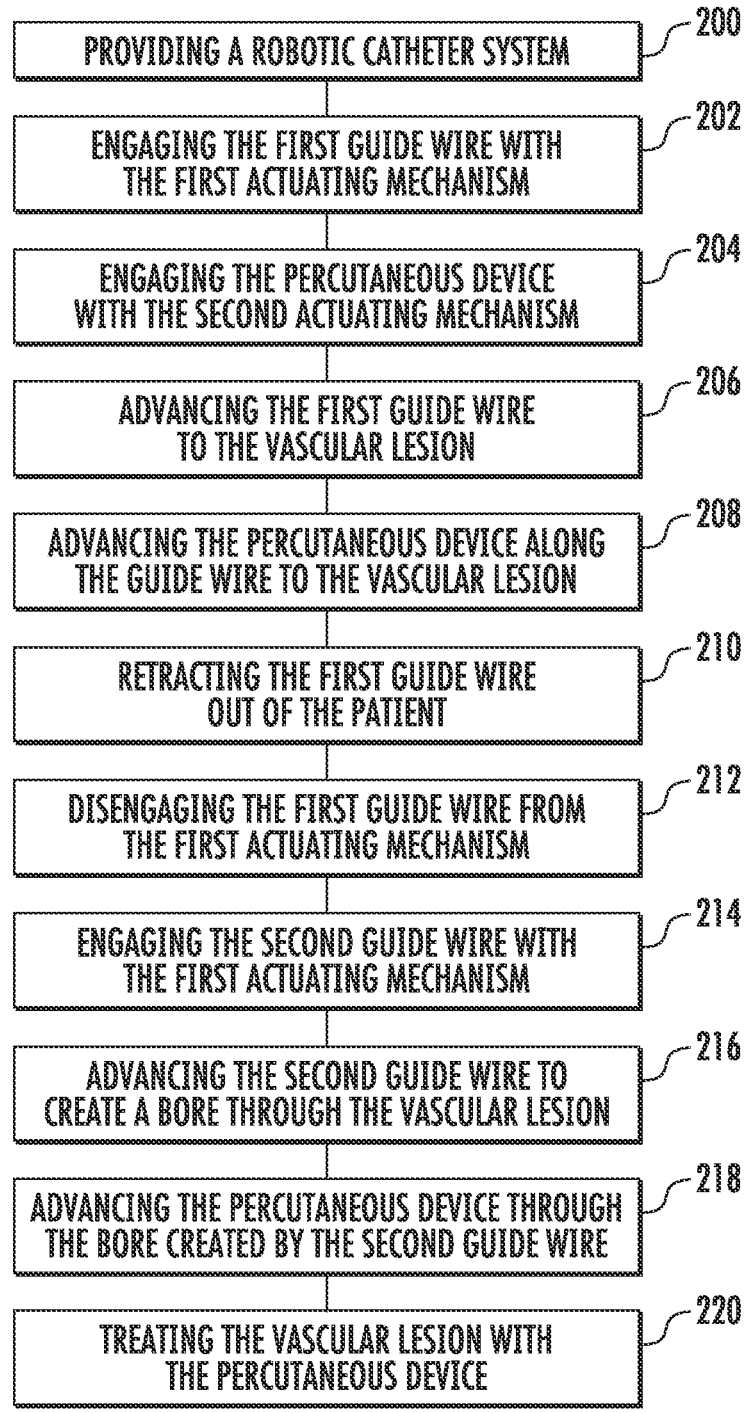
FIG. 13 is a flow-diagram showing operation of a robotic catheter system during treatment of a vascular lesion within a patient according to an exemplary embodiment.

FIG. 13 shows a flow-diagram of the operation of a robotic catheter system during treatment of a vascular lesion within a patient according to an exemplary embodiment. At step 200, a robotic catheter system, such as catheter procedure system 10, is provided. In one embodiment, the robotic catheter system includes a first guide wire (e.g. guide wire 58), a second guide wire configured for occlusion traversal (e.g., guide wire 84), and a percutaneous device (e.g., a working catheter equipped with a stent, angioplasty balloon, etc., such as working catheter 60). The robotic catheter system also includes first and second actuating mechanism configured to engage and impart movement to the guide wires and the percutaneous device, respectively (e.g., guide wire actuating mechanism 50 and working catheter actuating mechanism 52). The robotic catheter system also includes at least one control, such as controls 16, operative to allow the user to control the actuating mechanisms of the robotic catheter system. In other embodiments, the robotic catheter system may be any of the embodiments of catheter procedure system 10 discussed above and/or may include any combination of features or elements discussed above.

At step 202, the first guide wire is engaged by the first actuating mechanism, and at step 204, the percutaneous device is engaged by the second actuating mechanism. At step 206, the first guide wire is advanced to the vascular lesion via the first actuating mechanism in response to the user's operations of at least one control. At step 208, the percutaneous device is advanced to the vascular lesion via the second actuating mechanism along the first guide wire in response to the user's operations of at least one control. At step 210, the first guide wire is retracted back through the patient's vascular system and out of the patient via the first actuating mechanism in response to the user's operation of at least one control. At step 212, the first guide wire is disengaged from the first actuating mechanism, and, at step 214, the second guide wire is engaged by the first actuating mechanism.

At step 216, the second guide wire is advanced to the lesion and is advanced to create a bore through the lesion via the first actuating mechanism in response to the user's operation of at least one control. In one embodiment, the second guide wire is continuously rotated during advancement to create the bore through the lesion. In one embodiment, the user may define a rotation rate by operation of a control (e.g., a touch screen icon), and the second guide wire is rotated at the defined rotation rate during traversal through the lesion. In one embodiment, the second guide wire may be occlusion traversal guide wire 84, discussed above. In this embodiment, the coil diameter and coil angle of the helical shaped end section are changeable, and the robotic catheter system may include a third actuating mechanism operable to change, control or alter the coil diameter and coil angle of the helical shaped end section. In one embodiment, the user may operate a control to change the coil diameter and coil angle via the third actuating mechanism.

At step 218, the percutaneous device is advanced through the bore in the lesion created by the second guide wire via the second actuating mechanism in response to the user's operation of at least one control, and, at step 220, the lesion is treated using the percutaneous device (e.g., angioplasty balloon inflation, stent placement, etc.). In one embodiment, as discussed above, a single control may be operated by the user during occlusion traversal resulting in the advancement of both the second guide wire and the percutaneous device. Following treatment, the percutaneous device and the second guide wire may be retracted from the patient.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A method for operating a robotic catheter system during treatment of a vascular lesion within a patient comprising:
    providing a robotic catheter system, the robotic catheter system comprising:
        a first actuating mechanism configured to engage and to impart movement to a first percutaneous device; and
        a second actuating mechanism configured to engage and to impart movement to a second percutaneous device; and
        a control system controlling the first actuating mechanism and the second actuating mechanism, the control system configured to provide movement of the first percutaneous device and the second percutaneous device by operation of a single input control;
    receiving an operation of the single input control from a user during advancement of the first percutaneous device; and
    causing movement, responsive to the operation of the single input control, of both the first percutaneous device and the second percutaneous device such that the relative movement between the first percutaneous device and the second percutaneous device is substantially zero.

2. The method of claim 1, wherein the first actuating mechanism causes advancement of the first percutaneous device in response to the operation of the single input control and also causes rotation of the first percutaneous device during advancement of the first percutaneous device in response to the operation of the single input control.

3. The method of claim 2, wherein the first percutaneous device is rotated at a set rotation rate during advancement of the first percutaneous device.

4. The method of claim 2, wherein the first percutaneous device is advanced in the axial direction at a set rate in response to the operation of the single input control.

5. The method of claim 1, wherein the operation of the single input control controls the relative movement between the first percutaneous device and the second percutaneous device and one or more additional percutaneous devices.

6. The method of claim 1, wherein an end section of the second percutaneous device comprises a helical shaped section including a coil diameter and a coil angle, wherein the coil diameter and coil angle are changeable during the procedure.

7. The method of claim 6, wherein the robotic catheter system includes a third actuating mechanism configured to change the coil diameter and coil angle of the helical shaped section.

8. The method of claim 6, further comprising operating the single input control to change the coil diameter and the coil angle via the third actuating mechanism.

9. The method of claim 1, wherein the first percutaneous device is a guide wire and further wherein an end section of the guide wire comprises a plurality of helically disposed projections.

10. The method of claim 9, wherein the projections are expandable in the radial direction.

11. A method for operating a robotic catheter system during treatment of a vascular lesion within a patient comprising:
providing a robotic catheter system, the robotic catheter system comprising:
a first actuating mechanism configured to engage and to impart movement to a first percutaneous device; and
a second actuating mechanism configured to engage and to impart movement to a second percutaneous device; and
a control system controlling the first actuating mechanism and the second actuating mechanism, the control system configured to provide movement of the first percutaneous device and the second percutaneous device by operation of a single input control;
receiving an operation of the single input control from a user during advancement of the first percutaneous device; and
causing movement, responsive to the operation of the single input control, of both the first percutaneous device and the second percutaneous device, wherein the operation of the single input control controls relative movement between the first percutaneous and second percutaneous devices based on the operation of the single input control, wherein the relative movement includes movement of the first percutaneous device at a selected rate relative to movement of the second percutaneous device.

12. The method of claim 11, wherein the movement of the first percutaneous device at a selected rate relative to movement of the second percutaneous device includes axial movement of the first percutaneous device at a first rate and axial movement of the first percutaneous device at a second rate.

13. The method of claim 11, wherein the movement of the first percutaneous device at a selected rate relative to movement of the second percutaneous device includes axial movement of the first percutaneous device and rotational movement of the first percutaneous device at a second rate.

14. The method of claim 11, wherein the operation of the single input control controls the relative movement between the first percutaneous device and the second percutaneous device and one or more additional percutaneous devices.

15. The method of claim 11, wherein an end section of the second percutaneous device comprises a helical shaped section including a coil diameter and a coil angle, wherein the coil diameter and coil angle are changeable during the procedure.

16. The method of claim 15, wherein the robotic catheter system includes a third actuating mechanism configured to change the coil diameter and coil angle of the helical shaped section.

17. The method of claim 15, further comprising operating the single input control to change the coil diameter and the coil angle via the third actuating mechanism.

18. The method of claim 11, wherein the first percutaneous device is a guide wire and further wherein an end section of the guide wire comprises a plurality of helically disposed projections.

19. The method of claim 18, wherein the projections are expandable in the radial direction.

20. A method for operating a robotic catheter system during treatment of a vascular lesion within a patient comprising:
providing a robotic catheter system, the robotic catheter system comprising:
a first actuating mechanism configured to engage and to impart movement to a first percutaneous device; and
a second actuating mechanism configured to engage and to impart movement to a second percutaneous device; and
a control system controlling the first actuating mechanism and the second actuating mechanism, the control system configured to provide movement of the first percutaneous device and the second percutaneous device by operation of a single input control;
receiving an operation of the single input control from a user during advancement of the first percutaneous device; and
causing movement, responsive to the operation of the single input control, of both the first percutaneous device and the second percutaneous device, wherein the operation of the single input control causes axial movement of the first percutaneous and rotational movement of the second percutaneous devices based on the operation of the single input control.

* * * * *